US008026062B2

(12) United States Patent
Danenberg

(10) Patent No.: US 8,026,062 B2
(45) Date of Patent: Sep. 27, 2011

(54) METHOD OF DETERMINING A CHEMOTHERAPEUTIC REGIMEN BY ASSAYING GENE EXPRESSION IN PRIMARY TUMORS

(75) Inventor: Kathleen D. Danenberg, Altadena, CA (US)

(73) Assignee: Response Genetics, Inc., Los Angeles, CA (US)

( * ) Notice: Subject to any disclaimer, the term of this patent is extended or adjusted under 35 U.S.C. 154(b) by 439 days.

(21) Appl. No.: 11/731,128

(22) Filed: Mar. 30, 2007

(65) Prior Publication Data

US 2008/0160517 A1    Jul. 3, 2008

Related U.S. Application Data

(60) Division of application No. 09/998,333, filed on Dec. 3, 2001, now abandoned, which is a continuation-in-part of application No. 09/988,784, filed on Nov. 20, 2001, now Pat. No. 6,602,670, which is a continuation-in-part of application No. 09/879,217, filed on Jun. 13, 2001, now Pat. No. 7,005,278, which is a continuation-in-part of application No. 09/877,177, filed on Jun. 11, 2001, now Pat. No. 6,582,919, which is a continuation-in-part of application No. 09/877,178, filed on Jun. 11, 2001, now Pat. No. 7,049,059.

(60) Provisional application No. 60/250,120, filed on Dec. 1, 2000, provisional application No. 60/250,472, filed on Dec. 4, 2000.

(51) Int. Cl.
*C12Q 1/68* (2006.01)
*C12P 19/34* (2006.01)

(52) U.S. Cl. ......................... 435/6.1; 435/6.11; 435/6.12

(58) Field of Classification Search ......................... None
See application file for complete search history.

(56) References Cited

U.S. PATENT DOCUMENTS

| | | | |
|---|---|---|---|
| 4,830,969 A | 5/1989 | Holmes | |
| 4,843,155 A | 6/1989 | Chomczynski | |
| 5,128,247 A | 7/1992 | Koller | |
| 5,284,940 A | 2/1994 | Lin et al. | |
| 5,346,994 A | 9/1994 | Chomczynski | |
| 5,502,166 A | 3/1996 | Mishina | |
| 5,620,852 A | 4/1997 | Lin et al. | |
| 5,637,687 A | 6/1997 | Wiggins | |
| 5,643,767 A | 7/1997 | Fischetti et al. | |
| 5,654,179 A | 8/1997 | Lin | |
| 5,672,696 A | 9/1997 | Wang et al. | |
| 5,705,336 A | 1/1998 | Reed et al. | |
| 5,707,802 A | 1/1998 | Sandhu et al. | |
| 5,728,822 A | 3/1998 | Macfarlane | |
| 5,777,099 A | 7/1998 | Mehra | |
| 5,945,515 A | 8/1999 | Chomczynski | |
| 5,952,202 A | 9/1999 | Aoyagi et al. | |
| 5,989,857 A | 11/1999 | Mundschenk | |
| 6,010,700 A | 1/2000 | Richt | |
| 6,015,673 A | 1/2000 | Gonzalez et al. | |
| 6,033,860 A | 3/2000 | Lockhart et al. | |
| 6,043,354 A | 3/2000 | Hillebrand et al. | |
| 6,248,535 B1 | 6/2001 | Danenberg et al. | |
| 6,372,444 B1 * | 4/2002 | Powers et al. | ................. 435/7.23 |
| 6,376,210 B1 * | 4/2002 | Yuan | ................. 435/18 |
| 6,448,041 B1 | 9/2002 | Wolven et al. | |
| 6,582,919 B2 | 6/2003 | Danenberg | |
| 6,759,217 B2 | 7/2004 | Kopreski | |
| 7,049,059 B2 * | 5/2006 | Danenberg | ................. 435/5 |

FOREIGN PATENT DOCUMENTS

| | | |
|---|---|---|
| WO | 95/28489 | 10/1995 |
| WO | 97/05248 | 2/1997 |
| WO | 97/35034 | 9/1997 |
| WO | 98/41648 | 9/1998 |
| WO | 02/070750 | 9/2002 |

OTHER PUBLICATIONS

Johnston et al., "Thymidylate Synthase (TS) Expression from Formalin Fixed Paraffin Embedded (FFPE) Tissues Using Quantitative RT-PCR Correlates with Frozen Tissue Data and Predicts for Response to 5-Fluororuidine (5-FU) in Metastatic Colorectal Cancers," Proceedings of ASCO, 1999, vol. 18, Abstract No. 2383, printout pp. 1-3.*
Buck et al., "Design Strategies and Performance of Custom DNA Sequencing Primers," BioTechniques, Sep. 1999, vol. 27, pp. 528-536.*
Johnston et al., "Thymidylate Synthase Protein Expression in Primary Colorectal Cancer: Lack of Correlation With Outcome and Responses to Fluorouracil in Metastatic Disease Sites," Journal of Clinical Oncology, Mar. 2003, vol. 21, No. 5, pp. 815-819.*
Ardalan, B., et al., "*Thymidylate Synthase Gene Expression in Normal and Malignant Colorectal Tissues: Relation to in vivo Response and Survival*," Proceedings of the American Association for Cancer Research, vol. 37, Abstract No. 1376 (Mar. 1996).
Ardalan, B., et al., "*Thymidylate Synthase Gene Expression in Normal and Malignant Colorectal Tissues: Relation to in vivo Response and Survivial*," Proceedings of the American Association for Cancer Research 37: Abstract No. 1376 (1996).
Aschele, C., et al., "*Thymidylate Synthase Protein Expression in Primary Colorectal Cancer Compared with the Corresponding Distant Metastases and Relationship with the Clinical Response to 5-Fluorouracil*," Clinical Cancer Research, 6: 4797-4802 (2000).
Ausubel, F.M., ed., *Current Protocols in Molecular Biology*, John Wiley & Sons, Inc., vol. 1.; Strauss, W. M., "*Preparation of Genomic DNA from Mammalian Tissue*," Unit 2.2, pp. 2.2.1-2.2.3 (1998).
Ausubel, F.M., ed., *Current Protocols in Molecular Biology*, John Wiley & Sons, Inc., vol. 1.; Richards, E., et al., "*Preparation of Genomic DNA from Plant Tissue*," Unit 2.3, pp. 2.3.1-2.3.7 (1994).

(Continued)

Primary Examiner — Young J Kim
(74) Attorney, Agent, or Firm — Kenyon & Kenyon LLP

(57) ABSTRACT

The invention relates to a method for determining a chemotherapeutic regimen for an individual, comprising obtaining a mRNA sample from a primary tumor specimen; determining a gene expression level for a tumor gene determinant in the specimen; comparing the gene expression level for the tumor gene determinant with a predetermined threshold value for that gene; and providing a chemotherapeutic regimen comprising a chemotherapeutic agent appropriate for the tumor gene determinant to treat the tumor metastases.

7 Claims, 4 Drawing Sheets

OTHER PUBLICATIONS

Ausubel, F.M., ed., *Current Protocols in Molecular Biology*, John Wiley & Sons, Inc., vol. 1.;Wilson, K., "Preparation of Genomic DNA from Bacteria," Unit 2.4, pp. 2.4.1-2.4.5 (1994).

Banerjee, S.K., et al., "Microwave-Based DNA Extraction from Paraffin-Embedded Tissue for PCR Amplification," BioTechniques 18(5):768, 770, 772, 773 (1995).

Beck, A., et al., "A Role for Dihydropyrimidine Dehydrogenase and Thymidylate Synthase in Tumour Sensitivity to Fluorouracil," Eur J Cancer 30A(10):1517-1522 (1994).

Benhattar, J., et al., "p53 Mutations as a Possible Predictor of Response to Chemotherapy in Metastatic Colorectal Carcinomas," Int J Cancer (Pred Oncol) 69: 190-192 (1996).

Bresters, D., et al., "Detection of Hepatitis C Viral RNA Sequences in Fresh and Paraffin-Embedded Liver Biopsy Specimens of Non-A, Non-B Hepatitis Patients," J Hepat 15: 391-395 (1992).

Bresters, D., et al., "The Duration of Fixation Influences the Yield of HCV cDNA-PCR Products from Formalin-Fixed, Paraffin-Embedded Liver Tissue," J Virol Method 48: 267-272 (1994).

Chen, Z., et al., "Correlation of Cisplatin Sensitivity with Differential Alteration of EGFR Expression in Head and Neck Cancer Cells," Anticancer Res 20:899-902 (2000).

Chen, Peter W., et al., "Expression of MAGE Genes in Ocular Melanoma During Progression from Primary to Metastatic Disease," Clinical & Experimental Metastasis 15(5): 509-518 (1997).

Chirgwin, J., M., et al., "Isolation of Biologically Active Ribonucleic Acid from Sources Enriched in Ribonuclease," Biochem 18(24): 5294-5299 (1979).

Chomczynski, P., et al., "Single-Step Method of RNA Isolation by Acid Guanidinium Thiocyanate-Phenol-Chloroform Extraction," Analytical Biochem 162: 156-159 (1987).

Chomczynski, P., "A Reagent for the Single-Step Simultaneous Isolation of RNA, DNA and Proteins from Cell and Tissue Samples," BioTechniques 15(3): 532-534, 536-537 (1993).

Coombs, N. J., et al., "Optimisation of DNA and RNA Extraction from Archival Formalin-Fixed Tissue," Nucl Acids Res 27(16): i-iii (1999).

Culp, L. A., et al., "Tracking Prostate Carcinoma Micrometastasis to Multiple Organs Using Histochemical Marker Genes and Novel Cell Systems," Histology & Histopathology 16(3): 945-953 (2001).

Dakhama, A., et al., "Amplification of Human β-Actin Gene by the Reverse Transcripase-Polymerase Chain Reaction: Implications for Assessment of RNA from Formalin-Fixed, Paraffin-Embedded Material," J Histochem and Cytochem 44(10): 1205-1207 (1996).

David, L., et al., "c-erb B-2 Expression in Primary Gastric Carcinomas and Their Metastases," Modern Pathology 5(4): 384-390 (1992).

de Andrés, B., et al., "Improved Method for mRNA Extration from Paraffin-Embedded Tissues," BioTechniques 18(1): 42-43 (1995).

Di Renzo, M. Flavia, et al., "Overexpression and Amplification of the Met/HGF Receptor Gene During the Progression of Colorectal Cancer," Clinical Res 1(2): 147-154 (1995).

Dinjens, Winand N. M., "Frequency and Characterization of p53 Mutations in Primary and Metastatic Human Prostate Cancer," Int J Cancer 56(5): 630-633 (1994).

Eads, C. A., et al., "CpG Island Hypermethylation in Human Colorectal Tumors is Not Associated with DNA Methyltransferase Overexpression," Cancer Res 59: 2302-2306 (1999).

Edamoto, Y., et al., "Hepatitis C and B Virus Infections in Hepatocellular Carcinoma," Cancer 77(9): 1787-1791 (1996).

Etienne M.C., et al., "Response to Fluorouracil Therapy in Cancer Patients: The Role of Tumoral Dihydropyrimidine Dehydrogenase Activity," J Clinical Oncol 13(7):1663-1670 (1995).

Farrugia, D., et al., "A Pharmacodynamic (PD) Study of the Thymidylate, Synthase (TS) Inhibitor Tomudex™ in Advanced Colorectal Cancer (CRC)," Proceedings of the American Association for Cancer Research, Eighty-eighth Annual Meeting (Apr. 12-16, 1997), vol. 38, Abstract #4132 (1997).

Finke, J., et al., "An Improved Strategy and a Useful Housekeeping Gene for RNA Analysis from Formalin-Fixed, Paraffin-Embedded Tissues by PCR," BioTechniques 14(3): 448-453 (1993).

Gamberi, G., et al., "C-myc and c-fos in Human Osteosarcoma: Prognostic Value of mRNA and Protein expression," Oncol 55(6): 556-563 (1998).

Goldsworthy, S. M., et al., "Effects of Fixation on RNA Extraction and Amplification from Laser Capture Microdissected Tissue," Mol Carcinogenesis 25: 86-91 (1999).

Gorlick, et al., "Higher Levels of Thymidylate Synthase Gene Expression are Observed in Pulmonary as Compared with Hepatic Metastases of Colorectal Adenocarcinoma," J Clin Oncol 16(4): 1465-1469 (1998).

Greer, C. E., et al., "PCR Amplification from Paraffin-Embedded Tissues," Am J Clin Pathol 95(2): 117-124 (1991).

Gruber, A. D., et al., "Detection of Bovine Viral Diarrhea Virus RNA in Formalin-Fixed, Paraffin-Embedded Brain Tissue by Nested Polymerase Chain Reaction," J Virol Methods 43: 309-319 (1993).

Guerrero, R.B., et al., "Effects of Formalin Fixation and Prolonged Block Storage on Detection of Hepatitis C Virus RNA in Liver Tissue," Diag Mol Pathol 6(5): 277-281 (1997).

Heid, C. A. et al., "Real Time quantitative PCR," Genome Res 6: 986-994 (1996).

Hodges, E., et al., "Isolation of Nucleic Acid from Paraffin Embedded Tissue for PCR Amplification and Sequencing of TcR Vβ Genes," Leuk Res 19(3): 183-186 (1995).

Horie, N., et al., "Functional Analysis and DNA Polymorphism of the Tandemly Repeated Sequences in the 5' terminal Regulatory Region of the Human Gene for Thymidylate Synthase," Cell Structure and Function 20(3): 191-197 (1995).

Horikoshi, T., et al., "Quantitation of Thymidylate Synthase, Dihydrofolate Reductase, and DT-Diaphorase Gene Expression in Human Tumors using the Polymerase Chain Reaction," Cancer Res 52: 108-116 (1992).

Ilsuih, T. C. II., et al., "Novel, Ligation-Dependent PCR Assay for Detection of Hepatitis C Virus in Serum," J Clin Microbiol 34(3): 501-507 (1996).

Ichikawa, et al., "Expression of Dihydropyrimidine Dehydrogenase (DPD) and Thymidylate Synthase (TS) mRNA in Primary Tumor Predicts the Anti-Tumor Effect in 5-Fluorouracil (FU Based Chemotherapy for Gastrointestinal (GI) Cancer," Proceedings of the American Association for Cancer Research 42: Abstract No. 3326 (Mar. 2001).

Iwamoto, K. S., et al., "Feasibility of Using Decades-Old Archival Tissues in Molecular Oncology/Epidmiology," Am J Pathol 149(2): 399-406 (1996).

Jackman, A. L., et al., "Thymidylate Synthetase Inhibitors: Experimental and Clinical Aspects," Chapter 7 in Experimental and Clinical Progress in Cancer Chemotherapy, F.M. Muggia, ed., Martinus Nijhoff, Boston, pp. 155-210 (1985).

Jiang, Y.-H., et al., "A Rapid RT-PCR Method for Detection of Intact RNA in Formalin-Fixed Paraffin-Embedded Tissues," Nucl Acids Res 23(15): 3071-3072 (1995).

Kawakami, K., et al., "Polymorphic Tandem Repeats in the Thymidylate Synthase Gene is Associated with its Protein Expression in Human Gastrointestinal Cancers," Proceedings of the American Society of Clinical Oncology 17: Abstract No. 1128 (May 1998).

Keyomarsi, K., et al., "Mechanism of the Cytotoxic Synergism of Fluoropyrimidines and Folinic Acid in Mouse Leukemic Cells," J Biol Chem 263(28): 14402-14409 (1988).

Kiyosawa, K., et al., "Interrelationship of Blood Transfusion, Non-A, Non-B Hepatitis and Hepatocellular Carcinoma: Analysis by Detection of Antibody to Hepatitis C Virus," Hepatol 12(4): 671-675 (1990).

Koopmans, M., et al., "Optimization of Extraction and PCR Amplification of RNA Extracts from Paraffin-Embedded Tissue in Different Fixatives," J Virol Methods 43: 189-204 (1993).

Kornmann M. et al., "Thymidylate Synthase is a Predictor for Response and Resistance in Hepatic Artery Infusion Chemotherapy," Cancer Letters 118:29-35 (1997).

Lacroix, H., et al., "Overexpression of erb B-2 or EGF Receptor Proteins Present Early Stage Mammary Carcinoma is Detected Simultaneously in Matched Primary Tumors and Regional Metastases," Oncogene 4(2): 145-151 (1989).

Leichman, C. G., et al., "Quantitation of Intratumoral Thymidylate Synthase Expression Predicts for Disseminated Colorectal Cancer Response and Resistance to Protracted-Infusion Fluorouracil and Weekly Leucovorin,". J Clin Oncol 15(10): 3223-3229 (1997).

Lenz, et al., "*p53 Point Mutations and Thymidylate Synthase Messenger RNA levels in Disseminated Colorectal Cancer: An Analysis of Response and Survival*," Clin Cancer Res 4: 1243-1250 (1998).
Lenz, et al., "*p53 and Thymidylate Synthase Gene Expression in Untreated Stage II Colon Cancer: Association with Recurrence, Survival, and Site*" Clin Cancer Res 4: 1227-1234 (1998).
Lenz, et al., "*Thymidylate Synthase mRNA Level in Adenocarcinoma of the Stomach: a Predictor for Primary Tumor Response and Overall Survival*," J Clin Oncol 14: 176-182 (1995).
Lobban, E. D., et al., "*Uroplakin Gene Expression by Normal and Neoplastic Human Urothelium*," Am J Pathol 153(6): 1957-1967 (1998).
Lüscher, et al., "*The Pattern of Cytokine Gene Expression in Freshly Excised Human Metastatic Melanoma Suggests a State of Reversible Anergy of Tumor-Infiltrating Lymphocytes*," Int J Cancer 57(4): 612-619 (1994).
Macfarlane, D. E., et al., "*Introduction to Isolating RNA*," in RNA Isolation and Characterization Protocols, R. Rapley and D. L. Manning, eds., Humana Press (Series: Methods in Molecular Biology™), Totowa, N. J., pp. 1-6 (1998).
Marsh, S., et al., "*Ethnic Variation in the Thymidylate Synthase Enhancer Region Polymorphism among Caucasian and Asian Populations*," Genomics 58: 310-312 (1999).
Maurer, C. A., et al., "*Reduced Expression of the Metastasis Suppressor Gene KAII in Advanced Colon Cancer and Its Metastases*," Surgery 126(5): 869-880 (1999).
Mies, C., "*A Simple, Rapid Method for Isolating RNA from Paraffin-embedded Tissues for Reverse Transcription-Polymerase Chain Reaction (RT-PCR)*," J Histochem and Cytochem 42(6): 811-813 (1994).
Mirjolet, et al., "*Thymidylate Synthase Expression and Activity: Relation to S-phase Parameters and 5-fluorouracil Sensitivity*," Br J Cancer., Jul; 78(1): 62-8 (1998).
Miyauchi, et al., "*Further Study of Hepatitis C Virus RNA Detection in Formalin-Fixed, Paraffin-Embedded Liver Tissues by Ligation-Dependent Polymerase Chain Reaction*," Pathol Int 48: 428-432 (1998).
Mizuno, et al., "*RNA from Decades-Old Archival Tissue Blocks for Retrospective Studies*," Diag Mol Pathol 7(4): 202-208 (1998).
Mukhopadhyay, T., et al., "*Isolation of Total RNA from Tissues or Cell Lines*," in RNA Isolation and Characterization Protocols, R. Rapley and D. L. Manning, eds., Humana Press (Series: Methods in Molecular Biology™), Totowa, N.J., pp. 55-59 (1998).
Neskovic-Konstantinovic, Z., et al., "*Expression of Epidermal Growth Factor Receptor in Breast Cancer, from Early Stages to Advanced Disease*," J Exp Clin Cancer Res 18(3):347-355 (1999).
Newby J.C., et al., "*Expression of Epidermal Growth Factor Receptor and c-erbB2 during the Development of Tamoxifen Resistance in Human Breast Cancer*," Clin Cancer Res 3:1643-1651 (1997).
Nicholson, R.I., et al., "*Relationship Between EGF-R, c-erbB-2 Protein Expression and Ki67 Immunostaining in Breast Cancer and Hormone Sensitivity*," Eur J Cancer 29A(7):1018-1023 (1993).
Park, Y. N., et al., "*Detection of Hepatitis C Virus RNA Using Ligation-Dependent Polymerase Chain Reaction in Formalin-Fixed, Paraffin-Embedded Liver Tissues*," Am J Pathol 149(5): 1485-1491 (1996).
Rupp, G. M., et al., "*Purification and Analysis of RNA from Paraffin-Embedded Tissues*," BioTechniques 6(1): 56-60 (1988).
Salonga, et al., "*Colorectal Tumors Responding to 5-fluorouracil Have Low Gene Expression Levels of Dihydropyrimidine Dehydrogenase, Thymidylate Synthase, and Thymidine Phosphorylase*," Clin Cancer Res 6(4): 1322-1327 (2000).
Sambrook, J., et al., "*Isolation of High-Molecular-Weight DNA from Mammalian Cells*," in Molecular Cloning: A Laboratory Manual, $2^{nd}$ Ed., Cold Spring Harbor Laboratory Press, pp. 9.14-9.23 (1989).
Sander, C. A., et al., "*p53 Mutation is Associated with Progression in Follicular Lymphomas*," Blood 82(7): 1994-2004 (1993).
Santos, A. C., et al., "*Simultaneous Extraction of RNA and DNA from Paraffin-Embedded Tissues*," Trends in Genetics 9(7): 231 (1993).
Scartozzi, et al., "*Epidermal Growth Factor Receptor (EGFR) Status in Primary Colorectal Tumors Does Not Correlate with EGFR Expression in Related Metastatic Sites: Implications for Treatment with EGFR-Targeted Monoclonal Antibodies*," J Clin Oncol 22(23): 4772-4778 (2004).
Singh, R., et al., "*Influence of the Host Microenvironment on the Clonal Selection of Human Colon Carcinoma Cells During Primary Tumor Growth and Metastasis*," Clinical & Experimental Metastasis 15(2): 140-150 (1997).
Soguero, C., et al., "*Detection of Hepatitis C Virus RNA in More Than 20-Year Old Paraffin-Embedded Liver Tissue*," Laboratory Investigation 79(3): 365-366 (1999).
Sorg, I., et al., "*Detection of Borna Disease Virus RNA in Formalin-Fixed, Paraffin-Embedded Brain Tissues by Nested PCR*," J Clin Microbiol 33(4): 821-823 (1995).
Spears, C. P., et al., "In Vivo *Kinetics of Thymidylate Synthetase Inhibition in 5-Fluorouracil-Sensitive and—Resistant Murine Colon Adenocarcinomas,* " Cancer Res 42: 450-456 (1982).
Stanta, et al., "*RNA Extracted from Paraffin-Embedded Human Tissues is Amenable to Analysis by PCR Amplification*," BioTechniques 11(3): 304-308 (1991).
Stanta, et al., "*RNA Quantitative Analysis from Fixed and Paraffin-Embedded Tissues*," Methods in Mol Biol 86: 113-119 (1998).
Stanta, et al., "*RNA Extraction from Formalin-Fixed and Paraffin-Embedded Tissues*," Methods in Mol Biol 86: 23-26 (1998).
Swain, S. M., et al., "*Fluorouracil and High-Dose Leucovorin in Previously Treated Patients with Metastatic Breast Cancer*," J Clin Oncol 7(7): 890-899 (1989).
Wei, X., et al., "*Molecular Basis of the Human Dihydropyrimidine Dehydrogenase Deficiency and 5-Fluorouracil Toxicity*," J Clin Investigation 98(3): 610-615 (1996).
Wong, et al., "*Nuclear Thymidylate Synthase Expression, p53 Expression and 5FU Response in Colorectal Carcinoma*," Br J Cancer 85(12):1937-1943 (2001).
von Weizsäcker, F., et al., "*A Simple and Rapid Method for the Detection of RNA in Formalin-Fixed, Paraffin-Embedded Tissues by PCR Amplification*," Biochem and Biophys Res Comm 174(1): 176-180 (1991).
Yamada, H., et al., "*Thymidylate Synthase Gene Expression in Primary Colorectal Cancer and Metastatic Sites*," Clin Colorectal Cancer 1(3):169-173 (2001); discussion p. 174.
Yang, et al., "*A Comparative Study of E-cadherin mRNA Expression in Primary Tumors and Metastatic Foci of Gastric Cancer*," Zhonghua Zhong Li Za Zhi 27(1): Abstract only (2005).
Yu, et al., "*Comparative Study of Proteome Between Primary Cancer and Hepatic Metastatic Tumor in Colorectal Cancer*," World J Gastroenterol 10(18): 2652-2656 (2004).
Zeuthen, J., et al., "*Analysis of T Cell Receptor $\alpha\beta$ Variability in Tumor-Infiltrating Lymphocytes in Primary and Metastatic Melanoma*," Arch Immunol Ther Exp 43(2): 123-133 (1995).

* cited by examiner

| | Sample | From "Test" Reactions | | | From "Calibration" Reactions | | | | Uncorrected Gene Expression (UGE) | Known EGFR Values | Derivation of $K_{EGFR}$ | | Relative EGFR exp. |
|---|---|---|---|---|---|---|---|---|---|---|---|---|---|
| | | $C_T$ EGFR | $C_T$ β-ACTIN | $\Delta C_T$ | $2^{-\Delta C_T}$ | $C_T$ EGFR | $C_T$ β-ACTIN | $\Delta C_T$ | $2^{-\Delta C_T}$ | $2^{-\Delta C_T} / 2^{-\Delta C_T}$ | | K | $K_{EGF-R}$ (Avg. K) | |
| Experimental | Unknown 1 | 32.7 | 26.8 | 5.9 | 0.0167 | – | – | – | – | 0.525 | – | | 26.95 × $10^{-3}$ | 14.4 × $10^{-3}$ |
| | Unknown 2 | 32.88 | 26.43 | 6.45 | 0.0114 | – | – | – | – | 0.358 | – | | 26.95 × $10^{-3}$ | 9.66 × $10^{-3}$ |
| | Calib. RNA | – | – | – | – | 27.01 | 22.04 | 4.97 | 0.0319 | 0.0319/0.0319 = 1 | | | | |
| From Published Data | 60N | 31.61 | 23.86 | 7.75 | 0.00464 | – | – | – | – | 0.2117 | 5.70 × $10^{-3}$ | 26.95 × $10^{-3}$ | 26.95 × $10^{-3}$ | – |
| | 60T | 29.08 | 20.65 | 8.43 | 0.0029 | – | – | – | – | 0.1321 | 3.56 × $10^{-3}$ | 26.95 × $10^{-3}$ | 26.95 × $10^{-3}$ | – |
| | SF12A | 28.71 | 20.76 | 7.95 | 0.0040 | – | – | – | – | 0.184 | 4.97 × $10^{-3}$ | 26.95 × $10^{-3}$ | 26.95 × $10^{-3}$ | – |
| | SF12B | 24.69 | 19.87 | 4.82 | 0.0354 | – | – | – | – | 1.613 | 43.5 × $10^{-3}$ | 26.95 × $10^{-3}$ | 26.95 × $10^{-3}$ | – |
| | CTR11 | 24.03 | 16.3 | 7.73 | 0.0047 | – | – | – | – | 0.215 | 5.78 × $10^{-3}$ | 26.95 × $10^{-3}$ | 26.95 × $10^{-3}$ | – |
| | AdCol | 26.04 | 17.06 | 8.98 | 0.00198 | – | – | – | – | 0.090 | 2.43 × $10^{-3}$ | 26.95 × $10^{-3}$ | 26.95 × $10^{-3}$ | – |
| | Calib. RNA | – | – | – | – | 25.96 | 18.57 | 7.39 | 0.00596 | 0.00596/0.00596 = 1 | – | – | – | – |

FIG. 2  CHART ILLUSTRATING HOW TO CALCULATE EGFR EXPRESSION RELATIVE TO AN INTERNAL CONTROL GENE

| | Sample | From "Test" Reactions | | | From "Calibration" Reactions | | | | Uncorrected Gene Expression (UGE) | Published $DPD$ Values | Derivation of $K_{DPD}$ | | Corrected Relative DPD exp. |
|---|---|---|---|---|---|---|---|---|---|---|---|---|---|
| | | $C_T$ $DPD$ | $C_T$ $\beta$-ACTIN | $\Delta C_T$ | $2^{-\Delta C_T}$ | $C_T$ calib. RNA | $C_T$ $\beta$-ACTIN | $\Delta C_T$ | $2^{-\Delta C_T}$ | $2^{-\Delta C_T}/2^{-\Delta C_T}$ | | K | $K_{DPD}$ (Avg. K) | |
| Experimental | Unknown 1 | 25.05 | 19.84 | 5.21 | .027 | - | - | - | - | 4.47 | - | | $1.08 \times 10^{-3}$ | $4.83 \times 10^{-3}$ |
| | Unknown 2 | 28.18 | 18.76 | 9.42 | .0015 | - | - | - | - | 0.241 | - | | $1.08 \times 10^{-3}$ | $0.2608 \times 10^{-3}$ |
| | Calib. RNA | - | - | - | - | 26.92 | 19.55 | 7.37 | .006 | 0.006/0.006 = 1 | | | | $1.08 \times 10^{-3}$ |
| From Published Data | A | 31.04 | 24.56 | 6.49 | .0111 | - | - | - | - | 2.45 | $2.7 \times 10^{-3}$ | $1.10 \times 10^{-3}$ | $1.08 \times 10^{-3}$ | - |
| | B | 27.95 | 20.5 | 7.45 | .0057 | - | - | - | - | 1.26 | $1.2 \times 10^{-3}$ | $1.08 \times 10^{-3}$ | $1.08 \times 10^{-3}$ | - |
| | C | 26.88 | 19.2 | 7.68 | .00488 | - | - | - | - | 1.07 | $1.1 \times 10^{-3}$ | $1.02 \times 10^{-3}$ | $1.08 \times 10^{-3}$ | - |
| | D | 33.32 | 22.88 | 10.44 | .00072 | - | - | - | - | 0.158 | $0.17 \times 10^{-3}$ | $1.08 \times 10^{-3}$ | $1.08 \times 10^{-3}$ | - |
| | E | 26.96 | 22.01 | 4.95 | .03235 | - | - | - | - | 7.12 | $7.3 \times 10^{-3}$ | $1.03 \times 10^{-3}$ | $1.08 \times 10^{-3}$ | - |
| | F | 25.44 | 21.4 | 4.04 | .0607 | - | - | - | - | 13.38 | $16 \times 10^{-3}$ | $1.2 \times 10^{-3}$ | $1.08 \times 10^{-3}$ | - |
| | Calib. RNA | - | - | - | - | 27.88 | 20.098 | 7.782 | 0.005 | 0.005/0.005 = 1 | - | - | - | - |

FIG. 3    CHART ILLUSTRATING HOW TO CALCULATE $DPD$ EXPRESSION RELATIVE TO AN INTERNAL CONTROL GENE

| | Sample | From "Test" Reactions | | | From "Calibration" Reactions | | | | Uncorrected Gene Expression (UGE) $2^{-\Delta C_T}/2^{-\Delta C_T}$ | Published TS Values | Derivation of $K_{TS}$ (Avg. K) | | Corrected Relative TS exp. |
|---|---|---|---|---|---|---|---|---|---|---|---|---|---|
| | | $C_T$ TS | $C_T$ β-ACTIN | $\Delta C_T$ | $2^{-\Delta C_T}$ | $C_T$ calib. RNA | $C_T$ β-ACTIN | $\Delta C_T$ | $2^{-\Delta C_T}$ | | | K | $K_{TS}$ | |
| Experimental | Unknown 1 | 26.14 | 19.35 | 6.79 | 0.00903 | — | — | — | — | 0.178 | — | | $12.6 \times 10^{-3}$ | $2.25 \times 10^{-3}$ |
| | Unknown 2 | 32.07 | 28.38 | 3.69 | 0.0748 | — | — | — | — | 1.33 | — | | $12.6 \times 10^{-3}$ | $16.758 \times 10^{-3}$ |
| | Calib. RNA | — | — | — | — | 27.94 | 23.79 | 4.15 | 0.0563 | 0.056/0.056 = 1 | | | | |
| From Published Data | L7 | 26.94 | 24.55 | 2.39 | 0.191 | — | — | — | — | 3.18 | $38.8 \times 10^{-3}$ | $12.2 \times 10^{-3}$ | $12.6 \times 10^{-3}$ | — |
| | L91 | 24.91 | 22.12 | 2.79 | 0.144 | — | — | — | — | 2.40 | $29.55 \times 10^{-3}$ | $12.31 \times 10^{-3}$ | $12.6 \times 10^{-3}$ | — |
| | L121 | 24.95 | 20.89 | 4.06 | 0.059 | — | — | — | — | 0.88 | $12.22 \times 10^{-3}$ | $13.88 \times 10^{-3}$ | $12.6 \times 10^{-3}$ | — |
| | L150 | 29.77 | 22.88 | 6.89 | 0.008 | — | — | — | — | 0.133 | $1.72 \times 10^{-3}$ | $12.93 \times 10^{-3}$ | $12.6 \times 10^{-3}$ | — |
| | L220 | 26.52 | 19.77 | 6.75 | 0.0092 | — | — | — | — | 0.153 | $1.89 \times 10^{-3}$ | $12.35 \times 10^{-3}$ | $12.6 \times 10^{-3}$ | — |
| | L164 | 26.81 | 21.21 | 5.6 | 0.0205 | — | — | — | — | 0.341 | $4.2 \times 10^{-3}$ | $12.31 \times 10^{-3}$ | $12.6 \times 10^{-3}$ | — |
| | Calib. RNA | — | — | — | — | 25.14 | 20.09 | 5.04 | 0.06 | 0.06/0.06 = 1 | — | — | — | — |

FIG. 4  CHART ILLUSTRATING HOW TO CALCULATE TS EXPRESSION RELATIVE TO AN INTERNAL CONTROL GENE

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 1
tgcgtctctt gccggaat                                                       18

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 2
ggctcaccct ccagaagctt                                               20

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 3
acgcattccc tgcctcggct g                                             21

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 4
aggacgcaag gagggtttg                                                19

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 5
gtccgccgag tccttactga                                               20

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 6
cagtgcctac agtctcgagt ctgccagtg                                     29

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 7
ggcctcggtg tgccttt                                                  17

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 8
gatgtgcgca atcatgtacg t                                             21

<210> SEQ ID NO 9
<211> LENGTH: 22
<212> TYPE: DNA
<213> ORGANISM: Artificial Sequence

```
<220> FEATURE:
<223> OTHER INFORMATION: Oligonucleotide Primer

<400> SEQUENCE: 9
aacatcgcca gctacgccct gc                                      22

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 10
accaccacgg ccgagcgg                                           18

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 11
tgagcgcggc tacagctt                                           18

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 12
tccttaatgt cacgcacgat tt                                      22
```

METHOD OF DETERMINING A CHEMOTHERAPEUTIC REGIMEN BY ASSAYING GENE EXPRESSION IN PRIMARY TUMORS

RELATED APPLICATIONS

This application is a divisional application of application Ser. No. 09/998,333, filed Dec. 3, 2001 now abandoned, which is a continuation-in-part of application Ser. No. 09/988,784, filed Nov. 20, 2001 now U.S. Pat. No. 6,602,670, which is a continuation-in-part of application Ser. No. 09/879,217, filed Jun. 13, 2001 now U.S. Pat. No. 7,005,278, which is a continuation-in-part of application Ser. No. 09/877,177, filed Jun. 11, 2001 now U.S. Pat. No. 6,582,919, which is a continuation-in-part of application Ser. No. 09/877,178, filed Jun. 11, 2001 now U.S. Pat. No. 7,049,059, and claims priority to Provisional Application Nos. 60/250,120, filed Dec. 1, 2000, and 60/250,472, filed Dec. 4, 2000, the entire contents of which are hereby incorporated by reference into this application.

FIELD OF THE INVENTION

The present invention relates to prognostic methods which are useful in medicine, particularly cancer chemotherapy.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate in the absence of these normal controls, thus forming a tumor.

When a tumor is found, the clinical objective is to destroy malignant cells selectively while mitigating any harm caused to normal cells in the individual undergoing treatment. Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes.

Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies. Therefore, it is of importance to assess the expression status of genetic determinants targeted by specific chemotherapeutic agents. For example, if a tumor expresses high levels of DNA repair genes, it is likely that the tumor will not respond well to low doses of DNA-damaging genotoxic agents. Thus, the expression status of genetic determinants of a tumor will help the clinician develop an appropriate chemotherapeutic regimen specific to the genetic repertoire of the tumor.

As the single most effective agent for the treatment of colon, head and neck, and breast cancers, the primary action of 5-fluorouracil (5-FU) is to inhibit thymidylate synthase activity (Moertel, C. G. New Engl. J. Med., 330:1136-1142, 1994). For more than 40 years the standard first-line treatment for colorectal cancer was the use of 5-FU alone, but it was supplanted as "standard of care" by the combination of 5-FU and CPT-11 (Saltz et al., Irinotecan Study Group. New England Journal of Medicine. 343:905-14, 2000). Recently, the combination of 5-FU and oxaliplatin has produced high response rates in colorectal cancers (Raymond et al., Semin. Oncol., 25:4-12, 1998). We have previously shown that advanced stage colorectal tumors expressing high levels of thymidylate synthase (TS) responded poorly when treated with 5-FU/leucovorin. Thus, the patients' survival was low compared to those without elevated TS expression. (Leichman et al., J. Clin Oncol., 15: 3223-3229, 1997).

The mechanism of action and the metabolic pathway of 5-FU have been intensively studied over the years to identify the most important biochemical determinants of the drug's anti-tumor activity. The ultimate goal was to improve the clinical efficacy of 5-FU by a) modulation of its intracellular metabolism and biochemistry and b) measuring response determinants in patients' tumors prior to therapy to predict which patients are most likely to respond (or not to respond) to the drug. Two major determinants emerged from these studies: 1) the identity of the target enzyme of 5-FU, thymidylate synthase (TS) and 2) the identity of the 5-FU catabolic enzyme, dihydropyrimidine dehydrogenase (DPD).

The first studies in the area of tumor response prediction to 5-FU based therapy centered on the target enzyme TS in colorectal cancer. Leichman et al (Leichman et al., J. Clin Oncol., 15:3223-3229, 1997) carried out a prospective clinical trial to correlate tumor response to 5-FU with TS gene expression as determined by RT-PCR in pre-treatment biopsies from colorectal cancers. This study showed: 1) a large 50-fold range of TS gene expression levels among these tumors, and 2) strikingly different levels of TS gene expression between responding and non-responding tumors. The range of TS levels of the responding groups ($0.5$-$4.1 \times 10^{-3}$, relative to an internal control) was narrower than that of the non-responding groups ($1.6$-$23.0 \times 10^{-3}$, relative to an internal control). The investigators determined a resulting "non-response cutoff" threshold level of TS expression above which there were only non-responders. Thus, patients with TS expression above this "non-response cutoff" threshold could be positively identified as non-responders prior to therapy. The "no response" classification included all therapeutic responses with <50% tumor shrinkage, progressing growth resulting in a >25% tumor increase and non-progressing tumors with either <50% shrinkage, no change or <25% increase. These tumors had the highest TS levels. Thus, high TS expression identifies particularly resistant tumors. TS expression levels above a certain threshold identified a subset of tumors not responding to 5-FU, whereas TS expression levels below this number predicted an appreciably higher response rate, yet did not specifically identify responding tumors.

Subsequent studies investigated the usefulness of DPD expression levels as a tumor response determinant to 5-FU treatment in conjunction with TS expression levels. DPD is a catabolic enzyme which reduces the 5,6 double bond of 5-FU, rendering it inactive as a cytotoxic agent. Previous studies have shown that DPD levels in normal tissues could influence the bio-availability of 5-FU, thereby modulating its pharmacokinetics and anti-tumor activity (Harris et al., Cancer Res., 50: 197-201, 1990). Additionally, evidence has been presented that DPD levels in tumors are associated with sensitivity to 5-FU (Etienne et al., J. Clin. Oncol., 13: 1663-1670, 1995; Beck et al., Eur. J. Cancer, 30: 1517-1522, 1994). Salonga et al, (Clin Cancer Res., 6:1322-1327, 2000, hereby incorporated by reference in its entirety) investigated gene expression of DPD as a tumor response determinant for 5-FU/leucovorin treatment in a set of tumors in which TS expression had already been determined. As with TS, the range of DPD expression among the responding tumors was relatively narrow ($0.6$-$2.5 \times 10^{-3}$, 4.2-fold; relative to an internal control) compared with that of the non-responding tumors (0.2-16×10⁻³, 80-fold; relative to an internal control). There were no responding tumors with a DPD expression greater than a threshold level of about 2.5×10⁻³. Furthermore, DPD and TS expression levels showed no correlation with one another, indicating that they are independently regulated genes. Among the group of tumors having both TS and DPD expression levels below their respective "non-response cut-off" threshold levels, 92% responded to 5-FU/leucovorin. Thus, responding tumors could be identified on the basis of low expression levels of DPD and TS.

DPD is also an important marker for 5-FU toxicity. It was observed that patients with very low DPD levels (such as in DPD Deficiency Syndrome; i.e. thymine uraciluria) undergoing 5-FU based therapy suffered from life-threatening toxicity (Lyss et al., Cancer Invest., 11: 2390240, 1993). Indeed, the importance of DPD levels in 5-FU therapy was dramatically illustrated by the occurrence of 19 deaths in Japan from an unfavorable drug interaction between 5-FU and an antiviral compound, Sorivudine (Diasio et al., Br. J. Clin. Pharmacol. 46, 1-4, 1998). It was subsequently discovered that a metabolite of Sorivudine is a potent inhibitor of DPD. This treatment resulted in DPD Deficiency Syndrome-like depressed levels of DPD which increased the toxicity of 5-FU to the patients (Diasio et al., Br. J. Clin. Pharmacol. 46, 1-4, 1998).

Thus, because of a) the widespread use of 5-FU protocols in cancer treatment, b) the important role of DPD expression in predicting tumor response to 5-FU and c) the sensitivity of individuals with DPD-Deficiency Syndrome to common 5-FU based treatments, it is clear that accurate determination of DPD expression levels prior to chemotherapy will provide an important benefit to cancer patients.

Another class of chemotherapeutic agents specifically inhibits tumor cell proliferation by attenuating mitogenic signaling through receptor tyrosine kinases (RTKs), in cells where RTKs are over active. (Drugs of the Future, 1992, 17, 119). Receptor tyrosine kinases (RTKs) are important in the transduction of mitogenic signals. RTKs are large membrane spanning proteins which possess an extracellular ligand binding domain for growth factors such as epidermal growth factor (EGF) and an intracellular portion which functions as a kinase to phosphorylate tyrosine amino acid residues on cytosol proteins, thereby mediating cell proliferation. Various classes of receptor tyrosine kinases are known based on families of growth factors which bind to different receptor tyrosine kinases. (Wilks, Advances in Cancer Research, 1993, 60, 43-73)

Class I kinases such as the EGFR family of receptor tyrosine kinases include the EGF, HER2-neu, erbB, Xmrk, DER and let23 receptors. These receptors are frequently present in common human cancers such as breast cancer (Sainsbury et al., Brit. J. Cancer, 1988, 58, 458; Guerin et al., Oncogene Res., 1988, 3, 21), squamous cell cancer of the lung (Hendler et al., Cancer Cells, 1989, 7, 347), bladder cancer (Neal et al., Lancet, 1985, 366), oesophageal cancer (Mukaida et al, Cancer, 1991, 68, 142), gastrointestinal cancer such as colon, rectal or stomach cancer (Bolen et al., Oncogene Res., 1987, 1, 149), leukaemia (Konaka et al., Cell, 1984, 37, 1035) and ovarian, bronchial or pancreatic cancer (European Patent Specification No. 0400586). As further human tumor tissues are tested for the EGF family of receptor tyrosine kinases it is expected that its widespread prevalence will be established in other cancers such as thyroid and uterine cancer.

Specifically, EGFR tyrosine kinase activity is rarely detected in normal cells whereas it is more frequently detectable in malignant cells (Hunter, Cell, 1987, 50, 823). It has been more recently shown that EGFR is overexpressed in many human cancers such as brain, lung squamous cell, bladder, gastric, breast, head and neck, oesophageal, gynaecological and thyroid tumours. (W J Gullick, Brit. Med. Bull., 1991, 47, 87). Receptor tyrosine kinases are also important in other cell-proliferation diseases such as psoriasis. EGFR disorders are those characterized by EGFR expression by cells normally not expressing EGFR, or increased EGFR activation leading to unwanted cell proliferation, and/or the existence of inappropriate EGFR levels. The EGFR is known to be activated by its ligand EGF as well as transforming growth factor-alpha (TGF-a).

Inhibitors of receptor tyrosine kinases EGFR are employed as selective inhibitors of the growth of mammalian cancer cells (Yaish et al. Science, 1988, 242, 933). For example, erbstatin, an EGF receptor tyrosine kinase inhibitor, reduced the growth of EGFR expressing human mammary carcinoma cells injected into athymic nude mice, yet had no effect on the growth of tumors not expressing EGFR. (Toi et al., Eur. J. Cancer Clin. Oncol., 1990, 26, 722). Various derivatives of styrene are also stated to possess tyrosine kinase inhibitory properties (European Patent Application Nos. 0211363, 0304493 and 0322738) and to be of use as anti-tumor agents. Two such styrene derivatives are Class I RTK inhibitors whose effectiveness has been demonstrated by attenuating the growth of human squamous cell carcinoma injected into nude mice (Yoneda et al., Cancer Research, 1991, 51, 4430). It is also known from European Patent Applications Nos. 0520722 and 0566226 that certain 4-anilinoquinazoline derivatives are useful as inhibitors of receptor tyrosine kinases. The very tight structure-activity relationships shown by these compounds suggests a clearly-defined binding mode, where the quinazoline ring binds in the adenine pocket and the anilino ring binds in an adjacent, unique lipophilic pocket. Three 4-anilinoquinazoline analogues (two reversible and one irreversible inhibitor) have been evaluated clinically as anticancer drugs. Denny, Farmaco 2001 January-February; 56(1-2):51-6. Recently, the U.S. FDA approved the use of the monoclonal antibody trastazumab (Herceptin®) for the treatment of HER2-neu overexpressing metastatic breast cancers. Scheurle, et al., Anticancer Res 20:2091-2096, 2000.

Chemotherapy against tumors often requires a combination of agents such as those described above. Accordingly, the identification and quantification of determinants of resistance or sensitivity to each single drug has become an important tool to design individual combination chemotherapy.

Moreover, the search for genetic differences between primary tumors and metastases has been intensely pursued. Differential gene expression between a tumor and its metastases not only underlies the mechanism of tumor metastasis, but more importantly to the clinician, it determines the efficacy of chemotherapeutic agents on the primary tumor and matched metastases. Whereas primary tumor specimens are generally available either as pre-treatment paraffin-embedded biopsies or as resection specimens, in many cases, and especially in earlier stages of cancer, metastases are not readily detectable and biopsy specimens of matched tumor metastases on which phenotypic analyses could be performed would thus not be available. Therefore, it is important to determine the degree of variation of gene expression between primary tumors and metastases. This information is vital in order to determine whether or not a particular chemotherapeutic would be an effective therapeutic against the both the primary tumor as well as the metastases.

To date there has been no reliable way of determining whether a particular chemotherapy directed toward the expression of a tumor gene determinant appropriate for a primary tumor is also appropriate for treating a metastsis. Currently, the only way to reach such a conclusion was to have a fresh or frozen tissue biopsy of both the primary tumor and its metastasis. This would require a biopsy of primary tumor and matching tumor metastases. Unfortunately, because tumor metastases are often difficult to reach by standard surgical procedures and often only at great risk to the patient, it was previously not possible to determine whether a treatment regiment for the primary tumor would be effective in treating the metastases. Moreover, post-mortem analysis of tumor metastasis samples immediately frozen or fixed for comparison to similarly fixed matching primary tumor samples comes too late for the patient.

Previously, there existed no method to accurately and systematically compare the expression of tumor gene determinants in both primary tumor and metastases available in pathological archives. Most patient derived pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

The use of frozen tissue by health care professionals as described in Leichman et al., and Reed et al., poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintaining frozen tissue integrity during transport using specialized couriers equipped with liquid nitrogen and dry ice, comes only at a great expense.

Moreover, routine biopsies generally comprise a heterogenous mix of stromal and tumorous tissue. Unlike with fresh or frozen tissue, FPE biopsy tissue samples are readily microdissected and separated into stromal and tumor tissue and therefore, offer an advantage over the use of fresh or frozen tissue. However, isolation of RNA from fixed tissue, and especially fixed and paraffin embedded tissue, results in highly degraded RNA, which is generally not thought to be applicable to gene expression studies.

We report here a significant association between levels of tumor determinant gene expression in primary tumor with expression of the same tumor determinant gene in matching metastases in archival samples. Accordingly, it is the object of the invention to provide a method of quantifying mRNA from primary tumor tissue in order to provide an early prognosis for genetically targeted chemotherapies to treat tumors throughout the patient's body.

SUMMARY OF THE INVENTION

The invention relates to a method for determining a chemotherapeutic regimen for an individual, comprising obtaining a mRNA sample from a primary tumor specimen; determining a gene expression level for a tumor gene determinant in the specimen; comparing the gene expression level for the tumor gene determinant with a predetermined threshold value for that gene; and providing a chemotherapeutic regimen comprising a chemotherapeutic agent appropriate for the tumor gene determinant to treat the tumor metastases.

The invention further relates to a method of determining whether a chemotherapeutic regimen comprising a chemotherapeutic agent appropriate for a tumor gene determinant in a primary tumor is appropriate for a tumor metastasis comprising, obtaining an mRNA sample from the primary tumor, determining an expression level of a tumor gene determinant, comparing the expression level of the tumor gene determinant with a predetermined threshold level and determining the chemotherapeutic regimen for the tumor metastsis.

The invention also provides a method of quantifying the amount of tumor gene determinant mRNA expression in fresh, frozen, fixed or fixed and paraffin-embedded (FPE) tissue relative to gene expression of an internal control in a primary tumor in order to determine whether an anti-metabolite, genotoxic, and/or receptor tyrosine kinase targeted gene expression based chemotherapeutic appropriate for treating the primary tumor is appropriate for treating a tumor metastasis.

The invention provides a method of quantifying the amount of DPD, TS and/or EGFR mRNA expression in fresh, frozen, fixed or fixed and paraffin-embedded (FPE) tissue relative to gene expression of an internal control in a primary tumor in order to determine whether an anti-metabolite, genotoxic, and/or receptor tyrosine kinase targeted gene expression based chemotherapeutic appropriate for treating the primary tumor is appropriate for treating a tumor metastasis.

The invention also provides a method of quantifying the amount of DPD, TS and/or EGFR mRNA expression in fresh, frozen, fixed or fixed and paraffin-embedded (FPE) tissue relative to gene expression of an internal control in a primary tumor in order to determine whether a 5-FU, platinum, and/or receptor tyrosine kinase targeted gene expression based chemotherapeutic appropriate for treating the primary tumor is appropriate for treating a tumor metastasis.

DESCRIPTION OF THE DRAWINGS

FIG. 2 is a chart illustrating how to calculate EGFR expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with known relative EGFR values determined by pre-TaqMan® technology. This is accomplished by multiplying UGE to a correction factor $K_{EGFR}$. The internal control gene in the figure is β-actin and the calibrator RNA is Human Liver Total RNA (Stratagene, Cat #735017).

FIG. 3 is a chart illustrating how to calculate DPD expression relative to an internal control gene. The chart contains data obtained with two test samples, (unknowns 1 and 2), and illustrates how to determine the uncorrected gene expression data (UGE) UCG. The chart also illustrates how to normalize UGE generated by the Taqman instrument with previously published DPD values. This is accomplished by multiplying UGE to a correction factor $K_{DPD}$. The internal control gene in the figure is β-actin and the calibrator RNA is Universal PE RNA; Cat #4307281, lot #3617812014 from Applied Biosystems.

FIG. 4 is a chart illustrating how to calculate TS expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with previously published TS values. This is accomplished by multiplying UGE to a correction factor $K_{TS}$. The internal control gene in the figure is β-actin and the calibrator RNA is Universal PE RNA, Cat #4307281, lot #3617812014 from Applied Biosystems.

DETAILED DESCRIPTION OF THE INVENTION

Definitions

Figure 1:
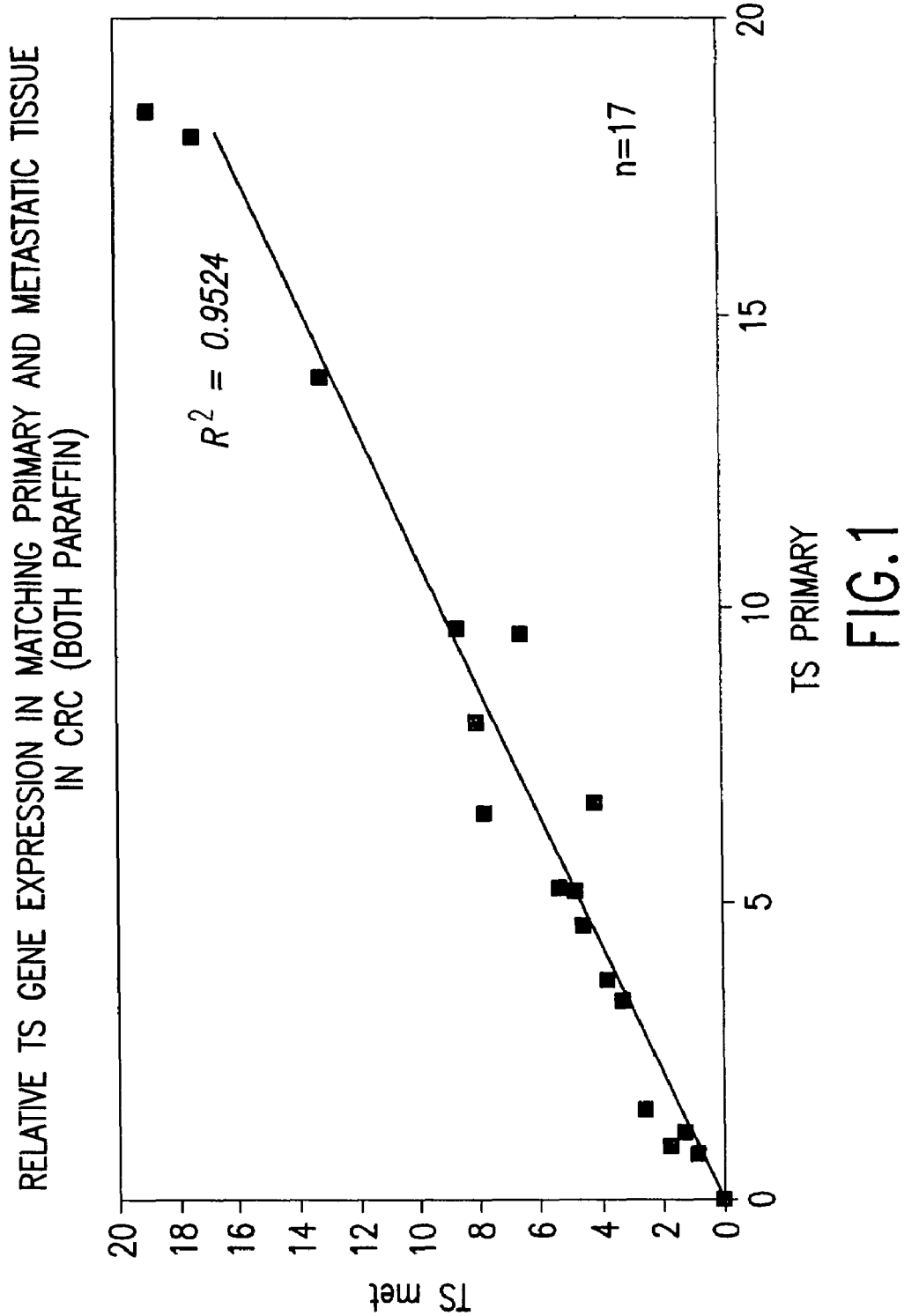
FIG. 1 is a graph showing relative TS gene expression in matching primary and metastatic issue in CRC. All values on the X and Y coordinates are times $10^3$.

A "tumor gene determinant" as used herein refers to a gene whose expression level is indicative of the effectiveness of a specific chemotherapeutic or class of chemotherapeutics. Such tumor gene determinants may include genes whose expression levels prognosticate the effectiveness of anti-metabolite chemotherapeutic agents. For example, as shown in U.S. Pat. Nos. 7,049,059 and 7,005,278 (both hereby incorporated by reference in their entirety), DPD and TS expression level can prognosticate the effectiveness of a 5-FU based chemotherapy. Other tumor gene determinants may include genes involved in DNA repair, whose expression levels prognosticate the effectiveness of genotoxic chemotherapeutic agents. Alternatively, as shown in U.S. Pat. Nos. 7,049,059 and 6,602,670 (both hereby incorporated by reference in their entirety) ERCC1 expression level can prognosticate the effectiveness of a genotoxic based chemotherapy. In another example, EGFR and Her2-neu expression as shown in U.S. Pat. No. 6,582,919 (hereby incorporated by reference in its entirety) can prognosticate the effectiveness of a receptor tyrosine kinase targeted chemotherapy. Furthermore, increased levels of the tumor determinant gene GST-pi have been found in drug resistant tumors, although the exact mechanism remains unclear.

A "predetermined threshold value" is determined by statistically correlating the expression level of a "tumor gene determinant" with the effectiveness of a course of treatment including a "chemotherapeutic agent specific for the tumor gene determinant" in question.

Generally, a threshold value may be determined by those of skill in the art from tissue samples given a method of determining tumor gene determinant expression in tissue samples with accompanying information including course of treatment and/or survival time. For example, the Mann-Whitney U test may be used to test for significant associations between the continuous test variable corrected relative tumor gene determinant expression and dichotomous variables (patient sex, age above and below the median age, presence of weight loss, presence of pleural effusion, tumor stage). The Kruskal-Wallis test may be used to test for significant differences in corrected relative tumor gene determinant expression within multiple groups (ECOG performance status, histopathology). Fisher's exact test may further be used for the analysis of categorical clinicopathological values including response and dichotomized corrected relative tumor gene determinant expression values.

Additionally, in order to determine a threshold value, Kaplan-Meier survival curves and the log rank test are used to analyze univariate distributions for survival and disease-free survival. The maximal chi-square method of Miller and Siegmund (Biometrics 1982; 38:1011-1016) and Halpern (Biometrics 1982; 38:1017-1023) can be adapted to determine which expression value best segregated patients into poor- and good prognosis subgroups (in terms of likelihood of surviving), with the log-rank test as the statistic used to measure the strength of the grouping. To determine a P value that would be interpreted as a measure of the strength of the association based on the maximal chi-square analysis, 1000 boot-strap-like simulations are used to estimate the distribution of the maximal chi-square statistics under the hypothesis of no association. (Biometrics 1982, 38:1017-1023). Cox's proportional hazards modeling of factors that are significant in univariate analysis is performed to identify which factors might have a significant influence on survival. SPSS version 10.0.5 software (SPSS Inc., Chicago Ill.) may be used for all statistical analyses.

The methodology for determining a threshold value for the tumor gene determinant DPD in fresh, frozen, fixed or fixed and paraffin-embedded (FPE) tissue relative to gene expression of an internal control is found in U.S. Pat. Nos. 7,005, 278, 6,905,821 and 6,956,111, all of which are hereby incorporated by reference in their entirety.

The methodology for determining a threshold value for the tumor gene determinant TS in fresh, frozen, fixed or fixed and paraffin-embedded (FPE) tissue relative to gene expression of an internal control is found in U.S. Pat. No. 7,049,059, which is hereby incorporated by reference in its entirety.

The methodology for determining a threshold value for the tumor gene determinant EGFR in fresh, frozen, fixed or fixed and paraffin-embedded (FPE) tissue relative to gene expression of an internal control is found in U.S. Pat. No. 6,582,919, which is hereby incorporated by reference in its entirety.

A "chemotherapeutic agent specific for the tumor gene determinant" refers to any chemotherapeutic agent which is known to target a cancer cell, and has an effectiveness correlating to the expression level of the tumor gene determinant. Knowledge of the physical interaction between the tumor gene determinant and the chemotherapeutic agent specific for the tumor gene determinant is not necessary so long there is a correlation between the expression of the tumor gene determinant and the effectiveness of the agent. Chemotherapeutic agents specific for a tumor gene determinant may include, but are not limited to, genotoxic therapies, anti-metabolite therapies and/or receptor tyrosine kinase based therapies.

"Genotoxic chemotherapeutic agents" are classes of chemotherapeutic agents that inflict damage on cellular DNA. Examples of genotoxic chemotherapeutic agents specific for the tumor gene determinant known to be involved in DNA repair are platinum-based chemotherapies which cause a "bulky adduct" of the DNA, wherein the primary effect is to distort the three-dimensional conformation of the double helix. Such compounds are meant to be administered alone, or together with other chemotherapies such as gemcitabine (Gem) or 5-Fluorouracil (5-FU). Platinum-based genotoxic chemotherapies comprises heavy metal coordination compounds which form covalent DNA adducts. Generally, these heavy metal compounds bind covalently to DNA to form, in pertinent part, cis-1,2-intrastrand dinucleotide adducts. Generally, this class is represented by cis-diamminedichloroplatinum (II) (cisplatin), and includes cis-diammine-(1,1-cyclobutanedicarboxylato)platinum(II) (carboplatin), cis-diammino-(1,2-cyclohexyl) dichloroplatinum(II), and cis-(1, 2-ethylenediamine)dichloroplatinum(II). Platinum first agents include analogs or derivatives of any of the foregoing representative compounds. Tumors currently manageable by platinum coordination compounds include testicular, endometrial, cervical, gastric, squamous cell, adrenocortical and small cell lung carcinomas along with medulloblastomas and neuroblastomas. Trans-Diamminedichloroplatinum (II) (trans-DDP) is clinically useless owing, it is thought, to the rapid repair of its DNA adducts. The use of trans-DDP as a chemotherapeutic agent herein likely would provide a compound with low toxicity in nonselected cells, and high relative toxicity in selected cells. In a preferred embodiment, the platinum compound is cisplatin. Many compounds are commonly given with platinum-based chemotherapy agents. For example, BEP (bleomycin, etoposide, cisplatin) is used for testicular cancer, MVAC (methotrexate, vinblastine, doxorubicin, cisplatin) is used for bladder cancer, MVP (mitomycin C, vinblastine, cisplatin) is used for non-small cell lung cancer treatment. Many studies have documented interactions between platinum-containing agents. Therapeutic drug synergism, for example, has been reported for many drugs potentially included in a platinum based chemotherapy. A very short list of recent references for this include the following: Okamoto et al., Urology 2001; 57:188-192.; Tanaka et al., Anticancer Research 2001; 21:313-315; Slamon et al., Seminars in Oncology 2001; 28:13-19; Lidor et al., Journal of Clinical Investigation 1993; 92:2440-2447; Leopold et al., NCI Monographs 1987;99-104; Ohta et al., Cancer Letters 2001; 162:39-48; van Moorsel et al., British Journal of Cancer 1999; 80:981-990.

Other genotoxic agents are those that form persistent genomic lesions and are preferred for use as chemotherapeutic agents in the clinical management of cancer. The rate of cellular repair of genotoxin-induced DNA damage, as well as the rate of cell growth via the cell division cycle, affects the outcome of genotoxin therapy. Unrepaired lesions in a cell's genome can impede DNA replication, impair the replication fidelity of newly synthesized DNA or hinder the expression of genes needed for cell survival. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions. A general class of genotoxic compounds that are used for treating many cancers and that are affected by levels of DNA repair gene expression are DNA alkylating agents and DNA intercalating agents. Psoralens are genotoxic compounds known to be useful in the photochemotherapeutic treatment of cutaneous diseases such as psoriasis, vitiligo, fungal infections and cutaneous T cell lymphoma. Harrison's Principles of Internal Medicine, Part 2 Cardinal Manifestations of Disease, Ch. 60 (12th ed. 1991). Another general class of genotoxic compounds, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; carminomycin (carubicin), daunomycin (daunorubicin), or 14-hydroxydaunomycin (adriamycin or doxorubicin); mitomycin A, B or C; mitoxantrone; plicamycin (nithramycin); and the like.

Still another general class of genotoxic agents that are commonly used and that alkylate DNA, are those that include the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds.

Yet another general class of genotoxic agents, members of which alkylate DNA, includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, trofosfamide and the like. Oligonucleotides or analogs thereof that interact covalently or noncovalently with specific sequences in the genome of selected cells can also be used as genotoxic agents, if it is desired to select one or more predefined genomic targets as the locus of a genomic lesion.

Another class of agents, members of which alkylate DNA, include the ethylenimines and methylmelamines. These classes include altretamine (hexamethylmelamine), triethylenephosphoramide (TEPA), triethylenethiophosphoramide (ThioTEPA) and triethylenemelamine, for example. Additional classes of DNA alkylating agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

"Anti-metabolite chemotherapeutic agents" are agents that interfere with nucleic acid synthesis, protein synthesis, and other vital metabolic processes. Examples of anti-metabolite chemotherapeutic agents specific for the tumor gene determinant known to be important in tumor cell metabolism include 5-FU, methotrexate, and ara-C.

"Receptor tyrosine kinase targeted chemotherapeutic agents" are agents that specifically inhibit signaling through receptor tyrosine kinases (RTKs) in cells where RTKs are over active. Examples of receptor tyrosine kinase targeted chemotherapeutic agents specific for tumor gene determinant known to be involved in receptor tyrosine kinase signaling include 4-anilinoquinazolines such as 6-acrylamido-4-anilinoquinazoline (Bonvini et al., Cancer Res. 2001 February 15;61(4):1671-7) and derivatives, erbstatin (Toi et al., Eur. J. Cancer Clin. Oncol., 1990, 26, 722.), Geldanamycin, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) which have been described generally as tyrosine kinase inhibitors. Also, Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Other agents targeting receptor tyrosine kinase signaling activity include antibodies that inhibit growth factor receptor biological function indirectly by mediating cytotoxicity via a targeting function. Antibodies complexing with the receptor activate serum complement and/or mediate antibody-dependent cellular cytotoxicity. The antibodies that bind the receptor can also be conjugated to a toxin (immunotoxins). Antibodies are selected that greatly inhibit the receptor function by binding the steric vicinity of the ligand binding site of the receptor (blocking the receptor), and/or that bind the growth factor in such a way as to prevent (block) the ligand from binding to the receptor. These antibodies are selected using conventional in vitro assays for selecting antibodies which neutralize receptor function. Antibodies that act as ligand agonists by mimicking the ligand are discarded by conducting suitable assays as will be apparent to those skilled in the art. For certain tumor cells, the antibodies inhibit an autocrine growth cycle (i.e. where a cell secretes a growth factor that then binds to a receptor of the same cell). Since some ligands, e.g. TGF-a, are found lodged in cell membranes, the antibodies serving a targeting function are directed against the ligand and/or the receptor. The cytotoxic moiety of the immunotoxin may be a cytotoxic drug or an enzymatically active toxin of bacterial or plant origin, or an enzymatically active fragment of such a toxin. Enzymatically active toxins and fragments thereof often used are diphtheria, nonbinding active fragments of diphtheria toxin, exotoxin (from *Pseudomonas aeruginosa*), ricin, abrin, modeccin, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, and enomycin. In another embodiment, the antibodies are conjugated to small molecule anticancer drugs. Conjugates of the monoclonal antibody and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl)hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the antibodies. Cytotoxic radiopharmaceuticals for treating cancer may be made by conjugating radioactive isotopes to the antibodies. The term "cytotoxic moiety" as used herein is intended to include such isotopes.

The exact formulation, route of administration and dosage of chemotherapeutic agents specific for a tumor gene determinant may be chosen by the individual physician in view of the patient's condition. (See e.g. Fingl et al., in The Pharmacological Basis of Therapeutics, 1975, Ch. 1 p. 1). It should be noted that the attending physician would know how and when to terminate, interrupt, or adjust administration due to toxicity, or organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

The invention primarily rests in the observation from archival pathological samples that expression of tumor gene determinants in primary tumors correlates with the expression of those tumor gene determinants in matching tumor metastases (a sample of a metastic cancer tissue derived from the same individual as the primary tumor sample) Accordingly, a chemotherapeutic regimen designed in view of the expression of tumor gene determinants in primary tumors is also appropriate for treating tumor metastases. Thus, the present invention allows one to correlate the effectiveness of a chemotherapeutic regimine treating a primary tumor to also treat the tumor metastases.

For example, a primary tumor having high level of EGFR mRNA expression is considered likely to be sensitive to receptor tyrosine kinase targeted chemotherapy. Thus, with the present invention, the tumor metastases of patients whose primary tumors express high levels, i.e. above a predetermined threshold value, of EGFR mRNA are considered also likely to be sensitive to receptor tyrosine kinase targeted chemotherapy. Conversely, the tumor metastases of patients whose primary tumors express low levels, i.e. below a predetermined threshold value, of EGFR mRNA are considered likely to be insensitive to receptor tyrosine kinase targeted chemotherapy.

Similarly, the tumor metastases of patients whose primary tumors express low levels i.e. below a predetermined threshold value, of TS mRNA are considered likely to be sensitive to TS targeted chemotherapy. Conversely, the tumor metastases of patients whose primary tumors express high levels, i.e. above a predetermined threshold value of TS mRNA are considered likely to be insensitive to TS-targeted chemotherapy.

Providing another example, the tumor metastases of patients whose primary tumors express low levels, i.e. below a predetermined threshold value, of DPD mRNA are considered likely to be sensitive to 5-FU based chemotherapy. Conversely, the tumor metastases of patients whose primary tumors express high levels, i.e. above a predetermined threshold value, of DPD mRNA are considered likely to be insensitive to 5-FU-based chemotherapy.

The methodology for determining the expression of a tumor gene determinant in fresh, frozen, fixed or fixed and paraffin-embedded (FPE) tissue relative to gene expression of an internal control is found in U.S. Pat. Nos. 7,005,278, 6,905,821 and 6,956,111, all of which are hereby incorporated by reference in their entirety (describing the methodology as it relates to DPD expression); in U.S. Pat. No. 7,049,059, which is hereby incorporated by reference in its entirety (describing the methodology as it relates to TS expression), and in U.S. Pat. No. 6,582,919, which is hereby incorporated by reference in its entirety (describing the methodology as it relates to EGFR expression).

This measurement of tumor gene determinant expression in a primary tumor may then be used for prognosis of a gene targeted chemotherapy to treat metastic tumors throughout the body. The tumor gene determinant can be any gene whose expression level is indicative of the effectiveness of a specific chemotherapeutic or class of chemotherapeutics. Preferably, the tumor gene determinants are TS, DPD and/or EGFR gene expression in a primary tumor used to treat tumor metastases in the liver. Preferably, the methods of the invention are applied to solid tumors, most preferably colorectal tumors.

Assessment of mRNA Expression

Solid or lymphoid primary tumors or portions thereof are surgically resected from the patient or obtained by routine biopsy. RNA isolated from frozen or fresh tumor samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

Tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. See Plenat et al., Ann Pathol 2001 January; 21(1):29-47. Non-embedded, fixed tissue as well as fixed and embedded tissue may also be used in the present methods. Solid supports for embedding fixed tissue are envisioned to be removable with organic solvents, for example, and allowing for subsequent rehydration of preserved tissue.

RNA is extracted from paraffin-embedded (FPE) tissue cells by any of the methods as described in U.S. Pat. No. 6,248,535, which is hereby incorporated by reference in its entirety. As used herein, FPE tissue means tissue that has been fixed and embedded in a solid removable support, such as storable or archival tissue samples. RNA may be isolated from an archival pathological sample or biopsy sample which is first deparaffinized. An exemplary deparaffinization method involves washing the paraffinized sample with an organic solvent, such as xylene. Deparaffinized samples can be rehydrated with an aqueous solution of a lower alcohol. Suitable lower alcohols include methanol, ethanol, propanols, and butanols. Deparaffinized samples may be rehydrated with successive washes with lower alcoholic solutions of decreasing concentration. Alternatively, the sample is simultaneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective amount of chaotropic agent" is chosen such that RNA is purified from a paraffin-embedded sample in an amount of greater than about 10-fold that isolated in the absence of a chaotropic agent. Chaotropic agents include: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

RNA is then recovered from the chaotropic solution by, for example, phenol chloroform extraction, ion exchange chromatography or size-exclusion chromatography. RNA may then be further purified using the techniques of extraction, electrophoresis, chromatography, precipitation or other suitable techniques known in the art.

The quantification of tumor gene determinant mRNA from purified total mRNA from fresh, frozen or fixed is preferably carried out using reverse-transcriptase polymerase chain reaction (RT-PCR) methods common in the art. Other methods of quantifying of mRNA include the use of molecular beacons and other labeled probes useful in multiplex PCR. Additionally, the present invention envisages the quantification of mRNA via use of a PCR-free systems employing, for example fluorescent labeled probes similar to those of the Invader® Assay (Third Wave Technologies, Inc.). Preferably, quantification of tumor gene determinants and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996; 6:986-994) and Gibson et al.(Genome Res 1996; 6:995-1001). The output of the ABI 7700 (TaqMan® Instrument) is expressed in Ct's or "cycle thresholds." With the TaqMan® system, a highly expressed gene having a higher number of target molecules in a sample generates a signal with fewer PCR cycles (lower Ct) than a gene of lower relative expression with fewer target molecules (higher Ct).

"House keeping" gene or "internal control" is any constitutively or globally expressed gene whose presence enables an assessment of tumor gene determinant mRNA levels. Such an assessment comprises a determination of the overall constitutive level of gene transcription and a control for variations in RNA recovery. "House-keeping" genes or "internal controls" can include, but are not limited to, the cyclophilin gene, β-actin gene, the transferrin receptor gene, GAPDH gene, and the like. Most preferably, the internal control gene is β-actin gene as described by Eads et al, Cancer Research 1999; 59:2302-2306.

A control for variations in RNA recovery requires the use of "calibrator RNA." The "calibrator RNA" is intended to be any available source of accurately pre-quantified control RNA.

As described above, a preferred quantification of gene expression uses a fluorescence based real time detection method. In a preferred TaqMan® system, three primers are used: a forward, and a reverse primer, and a dual labeled fluorogenic oligonucleotide probe that anneals specifically to the cDNA of the gene at issue. The fluorogenic probe anneals to the cDNA within the region between where the forward and the reverse primers anneal. Any suitable primers may used to assess the mRNA expression levels described above. They must provide an accurate assessment of DPD, TS and/or EGFR expression in a fixed paraffin embedded (FPE) tissue and are also preferably accurate for determining DPD, TS and/or EGFR expression levels in fresh or frozen tissue, i.e. they have high specificity for their target RNA. As mRNA derived from FPE samples is more fragmented relative to that of fresh or frozen tissue and it is therefore, more difficult to quantify.

In the preferred quantification system preferred primer for EGFR are SEQ ID NO: 1-3. Preferred primers for DPD are SEQ ID NO: 4-6. Preferred primers for TS are SEQ ID NO: 7-9. Preferred primers for β-actin are SEQ ID NO: 10-12.

The present invention resides in part in the finding that the amount of TS mRNA is correlated with resistance to 5-FU and oxaliplatin agents, respectively. Tumors expressing high levels of TS mRNA are considered likely to be resistant to platinum-based chemotherapy. Conversely, those tumors expressing low amounts of TS mRNA are likely to be sensitive to platinum-based chemotherapy. A patient's tumor TS mRNA expression status is judged by comparing it to a predetermined threshold expression level.

The invention provides a method of quantifying the amount of TS mRNA expression in fixed or fixed and paraffin-embedded (FPE) tissue relative to gene expression of an internal control. The present inventors have developed oligonucleotide primers that allow accurate assessment of TS gene expression in tissues that have been fixed or fixed and embedded. The invention provides oligonucleotide primers, TS-763F (SEQ ID NO: 7), TS-825R (SEQ ID NO: 8), or oligonucleotide primers substantially identical thereto, preferably to be used together with RNA extracted from fixed and paraffin embedded (FPE) tumor samples. This measurement of TS gene expression may then be used for prognosis of platinum-based chemotherapy "Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95-98% of the nucleotides. Selective hybridization exists when the hybridization is more selective than total lack of specificity. See, Kanehisa, Nucleic Acids Res., 12:203 213 (1984).

This embodiment of the invention further involves first determination of the content of TS mRNA in the sample by using a pair of oligonucleotide primers, preferably oligonucleotide primer pair TS-763F (SEQ ID NO: 7) and TS-825R (SEQ ID NO: 8), or oligonucleotides substantially identical thereto, for carrying out reverse transcriptase polymerase chain reaction. RNA is extracted from the FPE cells by any of the methods for mRNA isolation from such samples as described in U.S. Pat. No. 6,248,535, issued Jun. 19, 2001, and is hereby incorporated by reference in its entirety.

Briefly, the invention provides methods of purifying RNA from a biological tissue sample by heating the sample for about 5 to about 120 minutes at a temperature of between about 50 and about 100° C. in a solution of an effective concentration of a chaotropic agent. In one embodiment, the chaotropic agent is a guanidinium compound. RNA is then recovered from said solution. For example, RNA recovery can be accomplished by chloroform extraction.

In a method of the invention, RNA is isolated from an archival pathological sample. In one embodiment, a paraffin-embedded sample is first deparaffinized. An exemplary deparaffinization method involves washing the paraffinized sample with an organic solvent, preferably xylene. Deparaffinized samples can be rehydrated with an aqueous solution of a lower alcohol. Suitable lower alcohols include methanol, ethanol, propanols, and butanols. In one embodiment, deparaffinized samples are rehydrated with successive washes with lower alcoholic solutions of decreasing concentration. In another embodiment, the sample is simultaneously deparaffinized and rehydrated.

The deparaffinized samples can be homogenized using mechanical, sonic or other means of homogenization. In one embodiment, the rehydrated samples are homogenized in a solution comprising a chaotropic agent, such as guanidinium thiocyanate (also sold as guanidinium isothiocyanate).

The homogenized samples are heated to a temperature in the range of about 50 to about 100° C. in a chaotropic solution, comprising an effective amount of a chaotropic agent. In one embodiment, the chaotropic agent is a guanidinium compound. A preferred chaotropic agent is guanidinium thiocyanate.

RNA is then recovered from the solution by, for example, phenol chloroform extraction, ion exchange chromatography or size-exclusion chromatography.

The invention provides specific oligonucleotide primers pairs and oligonucleotide primers substantially identical thereto, that allow particularly accurate assessment of TS expression in FPE tissues. Preferable are oligonucleotide primers, TS-763F (SEQ ID NO: 7) and TS-825R (SEQ ID NO: 8), (also referred to herein as the oligonucleotide primer pair TS) and oligonucleotide primers substantially identical thereto. The oligonucleotide primers TS-763F (SEQ ID NO: 7) and TS-825R (SEQ ID NO: 8) have been shown to be particularly effective for measuring TS mRNA levels using RNA extracted from the FPE cells by any of the methods for mRNA isolation, for example as described Example 1.

This invention includes substantially identical oligonucleotides that hybridize under stringent conditions (as defined herein) to all or a portion of the oligonucleotide primer sequence of TS-763F (SEQ ID NO: 7), its complement, or TS-825R (SEQ ID NO: 8) or its complement.

Under stringent hybridization conditions, only highly complementary, i.e., substantially similar nucleic acid sequences as defined herein hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least about 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer TS-763F (SEQ ID NO: 7), its complement or TS-825R (SEQ ID NO: 8) or its complement.

Hybridization of the oligonucleotide primer to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5× SSC/5× Denhart's solution/1.0% SDS, and washing in 0.2× SSC/0.1% SDS at room temperature. Moderately stringent conditions include washing in 3× SSC at 42° C. The parameters of salt concentration and temperature can be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al., eds., Current Protocols in Molecular Biology, John Wiley and Sons (1994).

Oligonucleotide primers disclosed herein are capable of allowing accurate assessment of TS gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying TS gene expression levels in FPE tissue where previously there existed no way to assay TS gene expression using fixed tissues.

"Uncorrected Gene Expression (UGE)" as used herein refers to the numeric output of a tumor gene determinant expression relative to an internal control gene generated by the TaqMan® instrument. The equation used to determine UGE for EGFR, TS and DPD, expression is shown in Examples 3, 4, and 5 respectively and illustrated with sample calculations in FIGS. 2, 3, and 4. Example 6 provides equations for calculating the UGE for any tumor gene determinant, referred to herein as GENE X.

A further aspect of this invention provides a method to normalize uncorrected gene expression (UGE) values acquired from the TaqMan® instrument with "known relative gene expression" values derived from non-TaqMan® technology. Preferably, TaqMan® derived tumor gene determinant UGE values (such as but not limited to DPD, TS and/or EGFR UGE values) from a tissue sample are normalized to samples with known non-TaqMan® derived relative tumor gene determinant: βactin expression values. For example, TaqMan® derived DPD, TS and/or EGFR values from a tissue sample are normalized to samples with known non TaqMan® derived relative DPD, TS and/or EGFR:β-actin expression values.

"Corrected Relative Tumor Gene Determinant Expression" as used herein refers to normalized tumor gene determinant expression whereby UGE is multiplied with a tumor gene determinant specific correction factor ($K_{geneX}$), resulting in a value that can be compared to a known range of tumor gene determinant expression levels relative to an internal control gene. These numerical values also allow the determination of whether or not the "Corrected Relative Expression" of a particular tumor sample divided by the "Corrected Relative Expression" of a matching non-tumor sample (i.e., differential expression) falls above or below the "predetermined threshold" level. Example 6 illustrates these calculations in detail.

"Known relative gene expression" values are derived from previously analyzed tissue samples and are based on the ratio of the RT-PCR signal of a target gene to a constitutively expressed internal control gene (e.g. β-Actin, GAPDH, etc.). Preferably such tissue samples are formalin fixed and paraffin-embedded (FPE) samples and RNA is extracted from them according to the protocol described in Example 1. To quantify gene expression relative to an internal control, standard quantitative RT-PCR technology known in the art is used. Pre-TaqMan® technology PCR reactions are run for a fixed number of cycles (i.e., 30) and endpoint values are reported for each sample. These values are then reported as a ratio of tumor gene determinant expression to β-actin expression.

$K_{geneX}$ may be determined for an internal control gene other than β-actin and/or a calibrator RNA different than Human Liver Total RNA (Stratagene, Cat #735017). To do so, one must calibrate both the internal control gene and the calibrator RNA to tissue samples for which GeneX tumor gene determinant expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1. Such a determination can be made using standard pre-TaqMan®, quantitative RT-PCR techniques well known in the art. Upon such a determination, such samples have "known relative gene expression" levels of GeneX tumor gene determinant useful in the determining a new $K_{GeneX}$ specific for the new internal control and/or calibrator RNA as described in Example 3 (regarding $K_{EGFR}$).

"Corrected Relative EGFR Expression" as used herein refers to normalized EGFR expression whereby UGE is multiplied with a EGFR specific correction factor ($K_{EGFR}$), resulting in a value that can be compared to a known range of EGFR expression levels relative to an internal control gene. Example 3 and FIG. 2 illustrate these calculations in detail. $K_{EGFR}$ specific for EGFR, the internal control β-actin and calibrator Human Liver Total RNA (Stratagene, Cat #735017), is $26.95 \times 10^{-3}$.

$K_{EGFR}$ may be determined for an internal control gene other than β-actin and/or a calibrator RNA different than Human Liver Total RNA (Stratagene, Cat #735017). To do so, one must calibrate both the internal control gene and the calibrator RNA to tissue samples for which EGFR expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1. Such a determination can be made using standard pre-TaqMan®, quantitative RT-PCR techniques well known in the art. Upon such a determination, such samples have "known relative gene expression" levels of EGFR useful in the determining a new $K_{EGFR}$ specific for the new internal control and/or calibrator RNA as described in Example 3.

"Corrected Relative DPD Expression" as used herein refers to normalized DPD expression whereby UGE is multiplied with a DPD specific correction factor ($K_{DPD}$), resulting in a value that can be compared to a previously published range of values. FIG. 3 illustrates these calculations in detail.

$K_{DPD}$ may be determined for an internal control gene other than β-actin and/or a calibrator RNA different than Human Liver Total RNA (Stratagene, Cat #735017). To do so, one must calibrate both the internal control gene and the calibrator RNA to tissue samples for which DPD expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1. Such a determination can be made using standard pre-TaqMan®, quantitative RT-PCR techniques well known in the art. Upon such a determination, such samples have "known relative gene expression" levels of DPD useful in the determining a new $K_{DPD}$ specific for the new internal control and/or calibrator RNA as described in Example 5.

"Previously published" relative gene expression results are based on the ratio of the RT-PCR signal of a target gene to a constitutively expressed gene (β-Actin). In pre-TaqMan® technology studies, PCR reactions were run for a fixed number of cycles (i.e., 30) and endpoint values were reported for each sample. These values were then reported as a ratio of DPD expression to β-actin expression. Salonga, et al., Clinical Cancer Research, 6:1322-1327, 2000, which is hereby incorporated by reference in its entirety.

"Corrected Relative TS Expression" as used herein refers to normalized TS expression whereby UGE is multiplied with a TS specific correction factor ($K_{TS}$), resulting in a value that can be compared to a known range of TS expression levels relative to an internal control gene. Example 4 and FIG. 4 illustrate these calculations in detail. These numerical values allow the determination of whether the "Corrected Relative TS Expression" of a particular sample falls above or below the "predetermined threshold" level. The predetermined threshold level of Corrected Relative TS Expression to β-actin level is about $7.5 \times 10^{-3}$. $K_{TS}$ specific for TS, the internal control β-actin and calibrator Universal PE RNA; Cat #4307281, lot #3617812014 from Applied Biosystems, is $12.6 \times 10^{-3}$.

$K_{TS}$ may be determined for an internal control gene other than .beta.-actin and/or a calibrator RNA different than Universal PE RNA; Cat #4307281, lot #3617812014 from Applied Biosystems. To ado so, one must calibrate both the internal control gene and the calibrator RNA to tissue samples for which TS expression levels relative to that particular internal control gene have already been determined (i.e., "known relative gene expression" or "previously published"). Preferably such tissue samples are formalin fixed and paraffin-embedded (FPE) samples and RNA is extracted from them according to the protocol described in Example 1 and in U.S. Pat. No. 6,248,535, which is hereby incorporated by reference in its entirety. Such a determination can be made using standard pre-TaqMan®), quantitative RT-PCR techniques well known in the art. Upon such a determination, such samples have "known relative gene expression" levels of TS useful in the determining a new $K_{TS}$ specific for the new internal control and/or calibrator RNA as described in Example 4.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of colorectal tumors.

Pre-chemotherapy treatment tumor biopsies are usually available only as fixed paraffin embedded (FPE) tissues, generally containing only a very small amount of heterogeneous tissue. Such FPE samples are readily amenable to microdissection, so that tumor gene determinant expression, such as DPD, TS and/or EGFR gene expression, may be determined in tumor tissue uncontaminated with non-malignant stromal tissue. Additionally, comparisons can be made between non-malignant stromal and tumor tissue within a biopsy tissue sample, since such samples often contain both types of tissues.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.
A. Deparaffinization and Hydration of Sections:

(1) A portion of an approximately 10 mM section is placed in a 1.5 mL plastic centrifuge tube.
(2) 600 μL, of xylene are added and the mixture is shaken vigorously for about 10 minutes at room temperature (roughly 20 to 25° C.).
(3) The sample is centrifuged for about 7 minutes at room temperature at the maximum speed of the bench top centrifuge (about 10-20,000×g).
(4) Steps 2 and 3 are repeated until the majority of paraffin has been dissolved. Two or more times are normally required depending on the amount of paraffin included in the original sample portion.
(5) The xylene solution is removed by vigorously shaking with a lower alcohol, preferably with 100% ethanol (about 600 μL) for about 3 minutes.
(6) The tube is centrifuged for about 7 minutes as in step (3). The supernatant is decanted and discarded. The pellet becomes white.
(7) Steps 5 and 6 are repeated with successively more dilute ethanol solutions: first with about 95% ethanol, then with about 80% and finally with about 70% ethanol.
(8) The sample is centrifuged for 7 minutes at room temperature as in step.
(9) The supernatant is discarded and the pellet is allowed to dry at room temperature for about 5 minutes.
B. RNA Isolation with Phenol-Chloroform
(1) 400 μL guanidine isothiocyanate solution including 0.5% sarcosine and 8 μL dithiothreitol is added.
(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).
(3) The sample is then heated at about 95° C. for about 5-20 minutes. It is preferable to pierce the cap of the tube containing the sample with a fine gauge needle before heating to 95° C. Alternatively, the cap may be affixed with a plastic clamp or with laboratory film.
(4) The sample is then extracted with 50 μL 2M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.
(5) The solution is centrifuged for about 7 minutes at maximum speed. The upper (aqueous) phase is transferred to a new tube.
(6) The RNA is precipitated with about 10 μL glycogen and with 400 μL isopropanol for 30 minutes at −20° C.
(7) The RNA is pelleted by centrifugation for about 7 minutes in a benchtop centrifuge at maximum speed, the supernatant is decanted and discarded; and the pellet washed with approximately 500 μL of about 70 to 75% ethanol.
(8) The sample is centrifuged again for 7 minutes at maximum speed. The supernatant is decanted and the pellet air dried. The pellet is then dissolved in an appropriate buffer for further experiments (e.g., 50 pI. 5 mM Tris chloride, pH 8.0).

Example 2 mRNA Reverse Transcription and PCR Reverse Transcription

RNA was isolated from microdissected or non-microdissected formalin fixed paraffin embedded (FPE) tissue as illustrated in Example 1, or from fresh or frozen tissue by a single step guanidinium isocyanate method using the QuickPrep™ Micro mRNA purification kit (Amersham Pharmacia Biotech Inc., Piscataway, N.J.) according to the manufacturer's instructions. After precipitation with ethanol and centrifugation, the RNA pellet was dissolved in 50 ul of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 ml of the RNA solution with 25.5 ml of "reverse transcription mix" (see below). The reaction was placed in a thermocycler for 8 min. at 26° C. (for binding the random hexamers to RNA), 45 min. at 42° C. (for the M-MLV reverse transcription enzymatic reaction) and 5 min at 95° C. (for heat inactivation of DNAse).

"Reverse transcription mix" consists of 10 ul 5× buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5),1.25 ul RNA Guard 24,800 U/ml (RNAse inhibitor) (Porcine #27-0816, Amersham Pharmacia) and 2.5 ul MMLV 200 U/ul (Life Tech Cat #28025-02).

Final concentrations of reaction components are: 50 mM Tris-HCl, pH 8.3, 75 mM KCl, 3 mM MgCl2, 1.0 mM dNTP, 1.0 mM DTT, 0.00375 mg/ml BSA, 0.62 U/ul RNA Guard and 10 U/ul MMLV.

PCR Quantification of mRNA Expression

Quantification of DPD, TS and/or EGFR cDNA and an internal control or house keeping gene (e.g., β-actin) cDNA was done using a fluorescence based real-time detection method (ABI PRISM 7700 or 7900 Sequence Detection System [TaqMan®], Applied Biosystems, Foster City, Calif.) as described by Heid et al., (Genome Res 1996; 6:986-994); Gibson et al., (Genome Res 1996; 6:995-1001). In brief, this method uses a dual labelled fluorogenic TaqMan® oligonucleotide probe, that anneals specifically within the forward and reverse primers. For EGFR, primer EGFR-1773 (SEQ ID NO: 3), $T_M=70°$ C. was used. For DPD, primer TaqMan probe DPD 3a (SEQ ID NO: 6) was used. For TS, primer TaqMan probe TS-781 (SEQ ID NO: 9) was used. For β-actin, TaqMan probe β-actin-611 (SEQ ID NO: 10) was used.

Laser stimulation within the capped wells containing the reaction mixture causes emission of a 3'quencher dye (TAMRA) until the probe is cleaved by the 5' to 3'nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number of the sequence of interest with the starting copy number of the internal control gene provides a relative gene expression level. TaqMan® analyses yield levels that are expressed as ratios between two absolute measurements (gene of interest: internal control gene).

The PCR reaction mixture consisted 0.5 ml of the reverse transcription reaction containing the cDNA prepared as described above, 600 nM of each forward and reverse oligonucleotide primers, 200 nM TaqMan® probe primer, 5 U AmpliTaq Gold Polymerase, 200 mM each dATP, dCTP, dGTP, 400 mM dTTP, 5.5 mM MgCl₂, and 1× Taqman Buffer A containing a reference dye, to a final volume of less than or equal to 25 ml (all reagents Applied Biosystems, Foster City, Calif.).

For EGFR, the forward and reverse primers were respectively EGFR-1753-F (SEQ ID NO: 1) and EGFR-R-1823R (SEQ ID NO: 2) and the TaqMan probe was TaqMan EGFR-1773 (SEQ ID NO: 3).

For DPD, the forward and reverse primers were respectively DPD 3a-51F (SEQ ID NO: 4) and DPD 3a-13R (SEQ ID NO: 5) and the TaqMan probe was TaqMan DPD 3a (SEQ ID NO: 6).

For TS, the forward and reverse primers were respectively TS-763F (SEQ ID NO: 7) and TS-82R (SEQ ID NO: 8) and the TaqMan probe was TaqMan TS-781 (SEQ ID NO: 9).

For β-actin, the forward and reverse primers were respectively β-actin-592F (SEQ ID NO: 11) and β-actin-651R (SEQ ID NO: 12) and the TaqMan probe was TaqMan β-actin-611 (SEQ ID NO: 10).

Cycling conditions were, 95° C. for 10 min., followed by 45 cycles at 95° C. for 15 s and 60° C. for 1 min.

Example 3

Determining the Uncorrected Gene Expression (UGE) for EGFR

Two pairs of parallel reactions are carried out. The "test" reactions and the "calibration" reactions. FIG. 2. The EGFR amplification reaction and the β-actin internal control amplification reaction are the test reactions. Separate EGFR and β-actin amplification reactions are performed on the calibrator RNA template and are referred to as the calibration reactions. The TaqMan® instrument will yield four different cycle threshold (Ct) values: $Ct_{EGFR}$ and $Ct_{\beta\text{-}actin}$ from the test reactions and $Ct_{EGFR}$ and $Ct_{\beta\text{-}actin}$ from the calibration reactions. The differences in Ct values for the two reactions are determined according to the following equation:

$$DCt_{test}=Ct_{EGFR}-Ct_{\beta\text{-}actin} \text{ (From the ``test'' reaction)}$$

$$DCt_{calibrator}=Ct_{EGFR}-Ct_{\beta\text{-}actin} \text{ (From the ``calibration'' reaction)}$$

Next the step involves raising the number 2 to the negative DCt, according to the following equations.

$$2^{-DCt}{}_{test} \text{ (From the ``test'' reaction)}$$

$$2^{-DCt}{}_{calibrator} \text{ (From the ``calibration'' reaction)}$$

In order to then obtain an uncorrected gene expression for EGFR from the TaqMan® instrument the following calculation is carried out:

$$\text{Uncorrected gene expression (UGE) for EGFR}=2^{-DCt_{test}}/2^{-DCt_{calibrator}}$$

Normalizing UGE with Known Relative EGFR Expression Levels

The normalization calculation entails a multiplication of the UGE with a correction factor ($K_{EGFR}$) specific to EGFR and a particular calibrator RNA. A correction factor $K_{EGFR}$ can also be determined for any internal control gene and any accurately pre-quantified calibrator RNA. Preferably, the internal control gene β-actin and the accurately pre-quantified calibrator RNA, Human Liver Total RNA (Stratagene, Cat #735017), are used. Given these reagents, correction factor $K_{EGFR}$ equals 1.54.

Normalization is accomplished using a modification of the DCt method described by Applied Biosystems, the TaqMan® manufacturer, in User Bulletin #2 and described above. To carry out this procedure, the UGE of 6 different FPE test tissues were analyzed for EGFR expression using the TaqMan® methodology described above. The internal control gene β-actin and the calibrator RNA, Human Liver Total RNA (Stratagene, Cat #735017) was used.

The already known relative EGFR expression level of each sample AG221, AG222, AG252, Adult Lung, PC3, AdCol was divided by its corresponding TaqMan® derived UGE to yield an unaveraged correction factor K.

$$K_{unaveraged} = \text{Known Values/UGE}$$

Next, all of the K values are averaged to determine a single $K_{EGFR}$ correction factor specific for EGFR, Stratgene Human Liver Total RNA (Stratagene, Cat #735017) from calibrator RNA, and β-actin.

Therefore, to determine the Corrected Relative EGFR Expression in an unknown tissue sample on a scale that is consistent with pre-TaqMan® EGFR expression studies, one merely multiplies the uncorrected gene expression data (UGE) derived from the TaqMan® apparatus with the $K_{EGFR}$ specific correction factor, given the use of the same internal control gene and calibrator RNA.

$$\text{Corrected Relative EGFR Expression} = UGE \times K_{EGFR}$$

A $K_{EGFR}$ may be determined using any accurately pre-quantified calibrator RNA or internal control gene. Future sources of accurately pre-quantified RNA can be calibrated to samples with known relative EGFR expression levels as described in the method above or may now be calibrated against a previously calibrated calibrator RNA such as Human Liver Total RNA (Stratagene, Cat #735017) described above.

For example, if a subsequent $K_{EGFR}$ is determined for a different internal control gene and/or a different calibrator RNA, one must calibrate both the internal control gene and the calibrator RNA to tissue samples for which EGFR expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{EGFR}$ specific to the different internal control gene and/or calibrator RNA.

Example 4

Determining the Uncorrected Gene Expression (UGE) for TS

Two pairs of parallel reactions are carried out. The "test" reactions and the "calibration" reactions. See FIG. 4. The TS amplification reaction and the β-actin internal control amplification reaction are the test reactions. Separate TS and β-actin amplification reactions are performed on the calibrator RNA template and are referred to as the calibration reactions. The TaqMan® instrument will yield four different cycle threshold (Ct) values: $Ct_{TS}$ and $Ct_{\beta-actin}$ from the test reactions and $Ct_{TS}$ and $Ct_{\beta-actin}$ from the calibration reactions. The differences in Ct values for the two reactions are determined according to the following equation:

$$DCt_{test} = Ct_{TS} - Ct_{\beta-actin} \text{ (From the "test" reaction)}$$

$$DCt_{calibrator} = Ct_{TS} - Ct_{\beta-actin} \text{ (From the "calibration" reaction)}$$

Next the step involves raising the number 2 to the negative DCt, according to the following equations.

$$2^{-DCt}_{test} \text{ (From the "test" reaction)}$$

$$2^{-DCt}_{calibrator} \text{ (From the "calibration" reaction)}$$

In order to then obtain an uncorrected gene expression for TS from the TaqMan® instrument the following calculation is carried out:

$$\text{Uncorrected gene expression (UGE) for TS} = 2^{-DCt}_{test}/2^{-DCt}_{calibrator}$$

Normalizing UGE with Known Relative TS Expression Levels

The normalization calculation entails a multiplication of the UGE with a correction factor ($K_{TS}$) specific to TS and a particular calibrator RNA. A correction factor $K_{TS}$ can also be determined for any internal control gene and any accurately pre-quantified calibrator RNA. Preferably, the internal control gene β-actin and the accurately pre-quantified calibrator RNA, Universal PE RNA; Cat #4307281, lot #3617812014 from Applied Biosystems are used. Given these reagents correction factor $K_{TS}$ equals $12.6 \times 10^{-3}$.

Normalization is accomplished using a modification of the DCt method described by Applied Biosystems, the TaqMan® manufacturer, in User Bulletin #2 and described above. To carry out this procedure, the UGE of 6 different previously published test tissues were analyzed for TS expression using the TaqMan® methodology described above. These tissue samples are described in Salonga, et al., Clinical Cancer Research, 6:1322-1327, 2000, which is hereby incorporated by reference in its entirety.

The internal control gene β-actin and the calibrator RNA, Universal PE RNA; Cat #4307281, lot #3617812014 from Applied Biosystems was used.

The previously published relative TS expression level of each sample L7, L91, L121, L150, L220, L164 was divided by its corresponding TaqMan® derived UGE to yield an unaveraged correction factor K. Salonga, et al., Clinical Cancer Research, 6:1322-1327, 2000, incorporated herein by reference in its entirety.

$$K_{averaged} = \text{Known Values/UGE}$$

Next, all of the K values are averaged to determine a single $K_{ERCC1}$ correction factor specific for TS, Applied Biosystems Universal PE RNA; Cat #4307281, lot #3617812014 calibrator RNA, and β-actin.

Therefore, to determine the Corrected Relative TS Expression in an unknown tissue sample on a scale that is consistent with pre-TaqMan® TS expression studies, one merely multiplies the uncorrected gene expression data (UGE) derived from the TaqMan® apparatus with the $K_{TS}$ specific correction factor, given the use of the same internal control gene and calibrator RNA.

$$\text{Corrected Relative TS Expression} = UGE \times K_{TS}$$

A $K_{TS}$ may be determined using any accurately pre-quantified calibrator RNA or internal control gene. Future sources of accurately pre-quantified RNA can be calibrated to samples with known relative ERCC1 expression levels as described in the method above or may now be calibrated against a previously calibrated calibrator RNA such as Universal PE RNA; Cat #4307281, lot #3617812014 from Applied Biosystems described above.

For example, if a subsequent $K_{TS}$ is determined for a different internal control gene and/or a different calibrator RNA, one must calibrate both the internal control gene and the calibrator RNA to tissue samples for which TS expression levels relative to that particular internal control gene have already been determined or published. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{TS}$ specific to the different internal control gene and/or calibrator RNA.

Example 5

Determining the Uncorrected Gene Expression (UGE) for DPD

Two pairs of parallel reactions are carried out. The "test" reactions and the "calibration" reactions. The DPD amplification reaction and the β-actin internal control amplification reaction are the test reactions. Separate β-actin and DPD amplification reactions are performed on the calibrator RNA and are referred to as the calibration reactions. The Taqman instrument will yield four different cycle threshold (Ct) values: $Ct_{DPD}$ and $Ct_{\beta-actin}$ from the test reactions and $Ct_{DPD}$ and $Ct_{\beta-actin}$ from the calibration reactions.

The differences in Ct values for the two reactions are determined according to the following equation:

$DCt_{test} = Ct_{DPD} - Ct_{\beta-actin}$ (From the "test" reaction)

$DCt_{calibrator} = Ct_{DPD} - Ct_{\beta-actin}$ (From the "calibration" reaction)

Next the step involves raising the number 2 to the negative DCt, according to the following equations.

$2^{-DCt}{}_{test}$ (From the "test" reaction)

$2^{-DCt}{}_{calibrator}$ (From the "calibration" reaction)

In order to then obtain an uncorrected gene expression for DPD from the Taqman instrument the following calculation is carried out:

Uncorrected gene expression (UGE) for DPD=
$2^{-DCt}{}_{test}/2^{-DCt}{}_{calibrator}$ Normalizing UGE with Previously Published Values The normalization calculation entails a multiplication of the UGE with a correction factor ($K_{DPD}$) specific to DPD and a particular calibrator RNA. The correction factor $K_{DPD}$ can be determined using any internal control gene and any accurately pre-quantified calibrator RNA. Preferably, the internal control gene β-actin and the accurately pre-quantified calibrator RNA, Universal PE RNA; Cat #4307281, lot #3617812014 from Applied Biosystems, are used.

Normalization is accomplished using modification of the DCt method described by Applied Biosystems, the Taqman manufacturer, in User Bulletin #2 and described above. To carry out this procedure, the UGE of 6 different previously published test tissues was analyzed for DPD expression using the Taqman methodology described above. The internal control gene β-actin and the calibrator RNA, Universal PE RNA; Cat #4307281, lot #3617812014 from Applied Biosystems was used.

The relative DPD expression level (PV) of each sample previously described in Salonga et al., which is hereby incorporated by reference in its entirety, L7, L91, L121, L150, L220 and L164, was divided by its corresponding Taqman derived UGE to yield an unaveraged correction factor K.

$K_{unaveraged} = PV/UGE$

Next, all of the K values are averaged to determine a single $K_{DPD}$ correction factor specific for DPD, Universal PE RNA; Cat #4307281, lot #3617812014 calibrator RNA and β-actin.

Therefore, to determine the Corrected Relative DPD Expression in an unknown tissue sample on a scale that is consistent with previously published pre-Taqman DPD expression studies, one merely multiplies the uncorrected gene expression data (UGE) derived from the Taqman apparatus with the $K_{DPD}$ specific correction factor, given the use of the same internal control gene and calibrator RNA.

Corrected Relative DPD Expression=UGE×$K_{DPD}$

A $K_{DPD}$ may be determined using any accurately pre-quantified calibrator RNA. Future sources of accurately pre-quantified RNA can be calibrated to published samples as described in the method above or may now be calibrated against a previously calibrated calibrator RNA such as Universal PE RNA; Cat #4307281, lot #3617812014 described above.

Example 6

Determining the Uncorrected Gene Expression (UGE) for GENE X Tumor Gene Determinant Two pairs of parallel reactions are carried out. The "test" reactions and the "calibration" reactions. The GENE X amplification reaction and the β-actin internal control amplification reaction are the test reactions. Separate GENE X and β-actin amplification reactions are performed on the calibrator RNA template and are referred to as the calibration reactions. The TaqMan® instrument will yield four different cycle threshold (Ct) values: $Ct_{GENE\ X}$ and $Ct_{\beta-actin}$ from the test reactions and $Ct_{GENE\ X}$ and $Ct_{\beta-actin}$ from the calibration reactions. The differences in Ct values for the two reactions are determined according to the following equation:

$DCt_{test} = Ct_{GENE\ X} - Ct_{\beta-actin}$ (From the "test" reaction)

$DCt_{calibrator} = Ct_{GENE\ X} - Ct_{\beta actin}$ (From the "calibration" reaction)

Next the step involves raising the number 2 to the negative DCt, according to the following equations.

$2^{-DCt}{}_{test}$ (From the "test" reaction)

$2^{-DCt}{}_{calibrator}$ (From the "calibration" reaction)

In order to then obtain an uncorrected gene expression for GENE X from the TaqMan® instrument the following calculation is carried out:

Uncorrected gene expression (UGE) for GENE X=
$2^{-DCt}{}_{test}/2^{-DCt}{}_{calibrator}$ Normalizing UGE with Known Relative GENE X Expression Levels The normalization calculation entails a multiplication of the UGE with a correction factor ($K_{GENE\ X}$) specific to GENE X and a particular calibrator RNA. A correction factor $K_{EGFR}$ can also be determined for any internal control gene and any accurately pre-quantified calibrator RNA. Preferably, the internal control gene β-actin and the accurately pre-quantified calibrator RNA, Human Liver Total RNA (Stratagene, Cat #735017), are used. The correction factor $K_{GENE\ X}$ is calculated.

Normalization is accomplished using a modification of the DCt method described by Applied Biosystems, the TaqMan® manufacturer, in User Bulletin #2 and described above. To carry out this procedure, the UGE of 6 different FPE test tissues are analyzed for GENE X expression using the TaqMan® methodology described above. The internal control gene β-actin and the calibrator RNA, Human Liver Total RNA (Stratagene, Cat #735017) is used.

Already known relative GENE X expression levels of each sample is divided by its corresponding TaqMan® derived UGE to yield an unaveraged correction factor K.

$$K_{unaveraged} = \text{Known Values/UGE}$$

Next, all of the K values are averaged to determine a single $K_{GENE\ X}$ correction factor specific for GENE X, Stratgene Human Liver Total RNA (Stratagene, Cat #735017) from calibrator RNA and β-actin.

Therefore, to determine the Corrected Relative GENE X Expression in an unknown tissue sample on a scale that is consistent with pre-TaqMan® GENE X tumor gene determinant expression studies, one merely multiplies the uncorrected gene expression data (UGE) derived from the TaqMan® apparatus with the $K_{GENE\ X}$ specific correction factor, given the use of the same internal control gene and calibrator RNA.

$$\text{Corrected Relative GENE X Expression} = \text{UGE} \times K_{GENE\ X}$$

A $K_{GENE\ X}$ may be determined using any accurately pre-quantified calibrator RNA or internal control gene. Future sources of accurately pre-quantified RNA can be calibrated to samples with known relative GENE X expression levels as described in the method above or may now be calibrated against a previously calibrated calibrator RNA such as Human Liver Total RNA (Stratagene, Cat #735017) described above.

For example, if a subsequent $K_{GENE\ X}$ is determined for a different internal control gene and/or a different calibrator RNA, one must calibrate both the internal control gene and the calibrator RNA to tissue samples for which GENE X expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{GENE\ X}$ specific to the different internal control gene and/or calibrator RNA.

Example 7

Correlation Between Tumor Gene Determinant Expression in Primary and Metastases

TS gene expressions were measured in 17 sets of tissues from paraffin-embedded primary colorectal cancers and matched liver metastases using quantitative real-time PCR (Taqman®). See FIG. 1. A method for mRNA isolation from such samples is described in U.S. Pat. No. 6,248,535, and is hereby incorporated by reference in its entirety.

Both the matching tumor sample and primary tumor sample have significantly similar expression levels of tumor gene markers. Preferably, the matching metastatic tumor sample is derived from a liver biopsy. Considering the primary tumors and the metastases as separate sets, the mean TS expressions were $5.16 \times 10^{-3}$ for primary tumors and $4.5 \times 10^{-3}$ for metastases. There was no significant difference between the gene expression values in the primary tumors and the metastases (p=0.73, F test). The correlation coefficient ($R^2$ value) between TS expression values in the sets of primary and metastatic tissue was 0.95. These data show that TS expression values in primary tumors accurately reflect those in metastatic tissues and thus, for patients with stage III tumors, therapy can be directed based on TS analyses in primary tumor tissue. Our findings have important practical implications for using TS values as a prognostic indicator in 5-FU based adjuvant therapy of colorectal cancer.

Example 8

Correlation Between TS Expression in Primary Tumor and Metastases

RNA was also isolated from 9 matched formalin-fixed, paraffin embedded, laser microdissected colorectal cancer primary tissues and liver metastases (total 18 specimens). TS mRNA expression, relative to expression of the housekeeping gene β-actin, was measured using a real time fluorescent dye quantitative RT-PCR system (TaqmanÒ). There was a significant linear correlation between TS mRNA expression in the primary and secondary tumors. (Spearman's rho correlation coefficient R=0.683, P=0.042 (two-tailed test)).

The invention claimed is:

1. A method for determining a chemotherapeutic regimen for treating a metastatic tumor in an individual having a primary and metastatic tumor comprising:
   (a) obtaining a primary tumor specimen;
   (b) determining a level of gene expression of Thymidylate Synthase (TS) in a primary tumor comprising
      (1) determining the level of TS mRNA in the specimen;
      (2) comparing said level of TS mRNA to a level of mRNA of an internal control gene; and
   (c) determining a chemotherapeutic regimen for treating the metastatic tumor in the individual based on the level of TS mRNA in the primary tumor specimen and a predetermined threshold level for the TS mRNA.

2. The method of claim 1, wherein determining the expression level of TS comprises a fluorescence based real-time detection method.

3. A method for determining a chemotherapeutic regimen for treating a metastatic tumor in an individual having a primary and metastatic tumor, comprising:
   (a) obtaining a fixed primary tumor specimen;
   (b) determining a level of gene expression for Thymidylate Synthase (TS) in the fixed tumor specimen comprising
      (1) isolating TS mRNA from the fixed tumor specimen by heating in the presence of a solution comprising an effective concentration of a chaotropic agent at a temperature in the range of about 50° C. to about 100° C. and recovering the mRNA from the chaotropic solution;
      (2) subjecting the mRNA to amplification using a pair of oligonucleotide primers capable of amplifying a region of TS to obtain an amplified sample;
      (3) determining the quantity of TS mRNA in the amplified sample;
   (c) comparing the quantity of TS mRNA from step (3) to a quantity of mRNA of an internal control gene; and
   (d) determining a chemotherapeutic regimen for treating the metastatic tumor based on the quantity of TS mRNA in the fixed primary tumor specimen and a predetermined threshold level for TS mRNA.

4. The method of claim 3, wherein determining the expression level of TS comprises a fluorescence based real-time detection method.

5. A method for determining a chemotherapeutic regimen for treating a metastatic tumor in an individual having a primary and metastatic tumor, comprising:
   (a) obtaining a fixed, paraffin-embedded (FPE) primary tumor specimen;
   (b) deparaffinizing the FPE specimen to obtain a deparaffinized sample;
   (c) determining a level of gene expression for Thymidylate Synthase (TS) in the deparaffinized sample comprising
      (1) isolating TS mRNA from the deparaffinized sample by heating in the presence of a solution comprising an effective concentration of a chaotropic agent at a temperature in the range of about 50° C. to about 100° C.;
      (2) subjecting the mRNA to amplification using a pair of oligonucleotide primers capable of amplifying a region of TS to obtain an amplified sample;

(3) determining the quantity of TS mRNA in the amplified sample;
(d) comparing the quantity of TS mRNA from step (3) to a quantity of mRNA of an internal control gene; and
(e) determining a chemotherapeutic regimen for treating the metastatic tumor based on the quantity of TS mRNA in the deparaffinized primary tumor sample and a predetermined threshold level for TS mRNA.

6. The method of claim 5, wherein the primer pair consists of a first oligonucleotide having the sequence set forth in SEQ ID: 7 or a sequence at least 90% identical thereto and a second oligonucleotide having the sequence set forth in SEQ ID NO: 8 or a sequence at least 90% identical thereto.

7. The method of any of claims 3-6, wherein the heating occurs at a temperature in the range of about 75° C. to about 100° C. for a period of about 5 to about 120 minutes.

* * * * *